(12) United States Patent
Gaut et al.

(10) Patent No.: US 10,060,925 B2
(45) Date of Patent: Aug. 28, 2018

(54) MIOX ANTIBODY AND ASSAY

(71) Applicant: Washington University, St. Louis, MO (US)

(72) Inventors: Joseph P. Gaut, St. Louis, MO (US); Jack Ladenson, St. Louis, MO (US); Dan Crimmins, St. Louis, MO (US); Vijay Modur, St. Louis, MO (US)

(73) Assignee: WASHINGTON UNIVERSITY, Saint Louis, MO (US)

( * ) Notice: Subject to any disclaimer, the term of this patent is extended or adjusted under 35 U.S.C. 154(b) by 254 days.

(21) Appl. No.: 14/903,956

(22) PCT Filed: Jul. 11, 2014

(86) PCT No.: PCT/US2014/046383
§ 371 (c)(1),
(2) Date: Jan. 8, 2016

(87) PCT Pub. No.: WO2015/006710
PCT Pub. Date: Jan. 15, 2015

(65) Prior Publication Data
US 2016/0216264 A1 Jul. 28, 2016

Related U.S. Application Data

(60) Provisional application No. 61/845,108, filed on Jul. 11, 2013.

(51) Int. Cl.
*G01N 33/573* (2006.01)
*C07K 16/40* (2006.01)
*G01N 33/68* (2006.01)

(52) U.S. Cl.
CPC ......... *G01N 33/573* (2013.01); *C07K 16/40* (2013.01); *G01N 33/6893* (2013.01); *C07K 2317/33* (2013.01); *C07K 2317/34* (2013.01); *C07K 2317/565* (2013.01); *G01N 2333/90241* (2013.01); *G01N 2800/347* (2013.01)

(58) Field of Classification Search
None
See application file for complete search history.

(56) References Cited

PUBLICATIONS

USPTO Training Materials 2009 "Written Description on Antibodies", p. 5, 37-48 (Year: 2009).*
Rudikoff et al (PNAS vol. 79, p. 1979-1983) (Year: 1982).*
Brown et al (J. Immuno. vol. 156 May, p. 3285-91) (Year: 1996).*
Vajdos et al. (J. Mol. Biol. , Jul. 5, 320(2): p. 415-28) (Year: 2002).*
Partial Supplementary European Search Report dated Mar. 7, 2017 from related European Patent Application Serial No. 14822351.4; 7 pgs.
Yang, B. et al., "High glucose-induced DNA-binding activities of nuclear factor of activated T cells 5 and carbohydrate response element binding protein to the myo-inositol oxygenase gene are inhibited by sorbinil in peripheral mononuclear cells from patients with type 1 diabetes mellitus and nephropathy," International J. Diabetes Mellitus, 2010, pp. 169-174, vol. 2, Elsevier Ltd.
Extended European Search Report dated Jun. 21, 2017 from related European Patent Application No. 14822351A; 16 pgs.
Arner et al., "Molecular cloning, expression, and characterization of myo-inositol oxygenase from mouse, rat, and human kidney," Biochemical and Biophysical Research Communications, 2004, pp. 1386-1392, vol. 324, No. 4.
Arner et al., "Expression of myo-inositol oxygenase in tissues susceptible to diabetic complications," Biochemical and Biophysical Research Communications, 2006, pp. 816-820, vol. 339, No. 3.
Arner et al., "myo-Inositol oxygenase: molecular cloning and expression of a unique enzyme that oxidizes myo-inositol and D-chiro-inositol," Biochem. Journal, 2001, pp. 313-320, vol. 360.
Crimmins et al., "ETRAP (efficient trapping and purification) of target protein polyclonal antibodies from GST-protein immune sera," Biotechnol. Appl. Biochem., 2010, pp. 127-138, vol. 57.
Gaut et al., "Expression of the Na+/K+-transporting ATPase gamma subunit FXYD2 in renal tumors," Modern Pathology, 2013, pp. 716-724, vol. 26.
Gaut et al., "Development of an Immunoassay for the Kidney-Specific Protein myo-Inositol Oxygenase, a Potential Biomarker of Acute Kidney Injury," Clinical Chemistry, 2014, pp. 747-757, vol. 60, No. 5.
Hu et al., "Identification of a novel kidney-specific gene downregulated in acute ischemic renal failure," Am J Physiol Renal Physiol, 2000, pp. F426-F439, vol. 279.
International Search Report and Written Opinion, related to PCT/US2014/046383, dated Oct. 28, 2014, 15 pgs.
Konvalinka, "myo-Inositol Oxygenase: A Novel Kidney-Specific Biomarker of Acute Kidney Injury?" Clinical Chemistry, 2014, pp. 708-710, vol. 60, No. 5.
Laterza et al., "Identification of Novel Brain Biomarkers," Clinical Chemistry, 2006, pp. 1713-1721, vol. 52, No. 9.
NCBI, Reference Sequence No. NP_060054.4, Dec. 5, 2012.
Noiri et al., "Urinary fatty acid-binding protein 1: an early predictive biomarker of kidney injury," Am J Physiol Renal Physiol, 2009, pp. F669-F679, vol. 296.
Prabhu et al., "Up-regulation of Human myo-Inositol Oxygenase by Hyperosmotic Stress in Renal Proximal Tubular Epithelial Cells," The Journal of Biological Chemistry, 2005, pp. 19895-19901, vol. 280, No. 20.
Thorsell et al., "Structural and Biophysical Characterization of Human myo-Inositol Oxygenase," The Journal of Biological Chemistry, 2008, pp. 15209-15216, vol. 283, No. 22.
Westhuyzen et al., "Measurement of tubular enzymuria facilitates early detection of acute renal impairment in the Intensive care unit," Nephrol Dial Transplant, 2003, pp. 543-551, vol. 18.

(Continued)

*Primary Examiner* — Changhwa J Cheu
(74) *Attorney, Agent, or Firm* — Polsinelli PC

(57) ABSTRACT

The invention relates to compositions and methods for detecting renal injury in a subject, such as proximal tubular injury associated with acute kidney injury.

17 Claims, 17 Drawing Sheets
(4 of 17 Drawing Sheet(s) Filed in Color)
Specification includes a Sequence Listing.

(56) References Cited

PUBLICATIONS

Xie et al., "Pathobiology of renal-specific oxidoreductase/myo-inositol oxygenase in diabetic nephropathy: its implications in tubulointerstitial fibrosis," American Journal of Physiology, 2010, pp. F1393-F1404, vol. 298, No. 6.

\* cited by examiner

```
         10          20          30          40          50          60
MKVTVGPDPS LVYRPDVDPE VAKDKASFRN YTSGPLLDRV FTTYKLMHTH QTVDFVRSKH
MKVTVGPDPS LVYRPDVDPE VAKDKASFR
         PS LVYRPDVDPE V
         70          80          90         100         110         120
AQFGGFSYKK MTVMEAVDLL DGLVDESDPD VDFPNSFHAF QTAEGIRKAH PDKDWFHLVG
                     GLVDESDPD VDFPNSF
        130         140         150         160         170         180
LLHDLGKVLA LFGEPQWAVV GDTFPVGCRP QASVVFCDST FQDNPDLQDP RYSTELGMYQ
                                       DST FQDNPDLQDP R
        190         200         210         220         230         240
PHCGLDRVLM SWGHDEYMYQ VMKFNKFSLP PEAFYMIRFH SFYPWHTGRD YQQLCSQQDL
        250         260         270         280
AMLPWVREFN KFDLYTKCPD LPDVDKLRPY YQGLIDKYCP GILSW
                                 QGLIDKYCP G
                             RPY YQGLIDKYC
```

FIG. 3C

SEQUENCE LISTING

```
<160> NUMBER OF SEQ ID NOS: 34

<210> SEQ ID NO 1
<211> LENGTH: 9
<212> TYPE: PRT
<213> ORGANISM: Artificial Sequence
<220> FEATURE:
<223> OTHER INFORMATION: SYNTHESIZED

<400> SEQUENCE: 1

Ser Gly Asn Ile His Asn Tyr Leu Ala
1               5

<210> SEQ ID NO 2
<211> LENGTH: 11
<212> TYPE: PRT
<213> ORGANISM: Artificial Sequence
<220> FEATURE:
<223> OTHER INFORMATION: SYNTHESIZED

<400> SEQUENCE: 2

Asn Ala Lys Thr Leu Ala Asp Gly Val Pro Ser
1               5                   10

<210> SEQ ID NO 3
<211> LENGTH: 9
<212> TYPE: PRT
<213> ORGANISM: Artificial Sequence
<220> FEATURE:
<223> OTHER INFORMATION: SYNTHESIZED

<400> SEQUENCE: 3

Gln His Phe Trp Ser Ile Pro Phe Thr
1               5

<210> SEQ ID NO 4
<211> LENGTH: 6
<212> TYPE: PRT
<213> ORGANISM: Artificial Sequence
<220> FEATURE:
<223> OTHER INFORMATION: SYNTHESIZED

<400> SEQUENCE: 4

Thr Ser Tyr Tyr Ile His
1               5

<210> SEQ ID NO 5
<211> LENGTH: 13
<212> TYPE: PRT
<213> ORGANISM: Artificial Sequence
<220> FEATURE:
<223> OTHER INFORMATION: SYNTHESIZED

<400> SEQUENCE: 5

Trp Ile Tyr Pro Gly Ser Gly Asn Ser Lys Tyr Asn Glu
```

<210> SEQ ID NO 6
<211> LENGTH: 9
<212> TYPE: PRT
<213> ORGANISM: Artificial Sequence
<220> FEATURE:
<223> OTHER INFORMATION: SYNTHESIZED

<400> SEQUENCE: 6

Tyr Tyr Cys Ala Arg Asp Gly Ser Thr
1               5

<210> SEQ ID NO 7
<211> LENGTH: 9
<212> TYPE: PRT
<213> ORGANISM: Artificial Sequence
<220> FEATURE:
<223> OTHER INFORMATION: SYNTHESIZED

<400> SEQUENCE: 7

Ser Lys Ser Val Ser Thr Ser Gly Tyr
1               5

<210> SEQ ID NO 8
<211> LENGTH: 11
<212> TYPE: PRT
<213> ORGANISM: Artificial Sequence
<220> FEATURE:
<223> OTHER INFORMATION: SYNTHESIZED

<400> SEQUENCE: 8

Leu Leu Ile Tyr Leu Ala Ser Asn Leu Glu Ser
1               5                   10

<210> SEQ ID NO 9
<211> LENGTH: 9
<212> TYPE: PRT
<213> ORGANISM: Artificial Sequence
<220> FEATURE:
<223> OTHER INFORMATION: SYNTHESIZED

<400> SEQUENCE: 9

Thr Tyr Tyr Cys Gln His Ser Arg Glu
1               5

<210> SEQ ID NO 10
<211> LENGTH: 6
<212> TYPE: PRT
<213> ORGANISM: Artificial Sequence
<220> FEATURE:
<223> OTHER INFORMATION: SYNTHESIZED

<400> SEQUENCE: 10

Thr Ser Tyr Trp Met His
1               5

<210> SEQ ID NO 11
<211> LENGTH: 13
<212> TYPE: PRT
<213> ORGANISM: Artificial Sequence
<220> FEATURE:
<223> OTHER INFORMATION: SYNTHESIZED

<400> SEQUENCE: 11

Leu Ile Asp Pro Ser Asp Ser Tyr Thr Asn Tyr Asn Gln
1               5                   10

```
<210> SEQ ID NO 12
<211> LENGTH: 9
<212> TYPE: PRT
<213> ORGANISM: Artificial Sequence
<220> FEATURE:
<223> OTHER INFORMATION: SYNTHESIZED

<400> SEQUENCE: 12

Tyr Tyr Cys Val Arg Thr Tyr Tyr His
 1               5

<210> SEQ ID NO 13
<211> LENGTH: 110
<212> TYPE: PRT
<213> ORGANISM: Artificial Sequence
<220> FEATURE:
<223> OTHER INFORMATION: SYNTHESIZED

<400> SEQUENCE: 13

Asp Ile Gln Met Thr Gln Ser Pro Ala Ser Leu Ser Ala Ser Val Gly
 1               5                  10                  15

Glu Thr Val Thr Ile Thr Cys Arg Thr Ser Gly Asn Ile His Asn Tyr
                20                  25                  30

Leu Ala Trp Tyr Gln Gln Lys Gln Gly Lys Ser Pro Gln Leu Leu Val
            35                  40                  45

Tyr Asn Ala Lys Thr Leu Ala Asp Gly Val Pro Ser Arg Phe Ser Gly
        50                  55                  60

Ser Gly Ser Gly Thr Gln Tyr Ser Leu Lys Ile Asn Ser Leu Gln Pro
65                  70                  75                  80

Glu Asp Phe Gly Ser Tyr Tyr Cys Gln His Phe Trp Ser Ile Pro Phe
                85                  90                  95

Thr Phe Gly Ser Gly Thr Lys Leu Glu Ile Lys Arg Ala Asp
            100                 105                 110

<210> SEQ ID NO 14
<211> LENGTH: 130
<212> TYPE: PRT
<213> ORGANISM: Artificial Sequence
<220> FEATURE:
<223> OTHER INFORMATION: SYNTHESIZED

<400> SEQUENCE: 14

Gln Val Gln Leu Gln Gln Ser Gly Pro Glu Leu Val Lys Pro Gly Ala
 1               5                  10                  15

Ser Val Lys Ile Ser Cys Lys Ala Ser Gly Tyr Ser Phe Thr Ser Tyr
                20                  25                  30

Tyr Ile His Trp Val Lys Gln Arg Pro Gly Gln Gly Leu Glu Trp Ile
            35                  40                  45

Gly Trp Ile Tyr Pro Gly Ser Gly Asn Ser Lys Tyr Asn Glu Lys Phe
        50                  55                  60

Lys Gly Lys Ala Thr Leu Thr Ala Asp Thr Ser Ser Ser Thr Ala Tyr
65                  70                  75                  80

Met Gln Leu Ser Ser Leu Thr Ser Glu Asp Ser Ala Val Tyr Tyr Cys
                85                  90                  95

Ala Arg Asp Gly Ser Thr Tyr Asn Trp Asn Phe Asp Val Trp Gly Thr
            100                 105                 110

Gly Thr Thr Val Thr Val Ser Ser Ala Lys Thr Thr Pro Pro Ser Val
        115                 120                 125
```

Tyr Pro
    130

<210> SEQ ID NO 15
<211> LENGTH: 111
<212> TYPE: PRT
<213> ORGANISM: Artificial Sequence
<220> FEATURE:
<223> OTHER INFORMATION: SYNTHESIZED

<400> SEQUENCE: 15

Asp Ile Val Val Thr Gln Ser Pro Ala Ser Phe Ala Val Ser Leu Gly
1               5                   10                  15

Gln Arg Ala Thr Ile Ser Cys Arg Ala Ser Lys Ser Val Ser Thr Ser
            20                  25                  30

Gly Tyr Ser Tyr Ile Asn Trp Tyr Gln Gln Lys Pro Gly Gln Pro Pro
        35                  40                  45

Lys Leu Leu Ile Tyr Leu Ala Ser Asn Leu Glu Ser Gly Val Pro Ala
    50                  55                  60

Arg Phe Ser Gly Ser Gly Ser Gly Thr Asp Phe Thr Leu Asn Ile His
65                  70                  75                  80

Pro Val Glu Glu Glu Asp Ala Ala Thr Tyr Tyr Cys Gln His Ser Arg
                85                  90                  95

Glu Leu Pro Leu Thr Phe Gly Ala Gly Thr Arg Leu Glu Leu Lys
            100                 105                 110

<210> SEQ ID NO 16
<211> LENGTH: 130
<212> TYPE: PRT
<213> ORGANISM: Artificial Sequence
<220> FEATURE:
<223> OTHER INFORMATION: SYNTHESIZED

<400> SEQUENCE: 16

Gln Val Gln Leu Gln Gln Pro Gly Ala Glu Leu Val Arg Pro Gly Thr
1               5                   10                  15

Ser Val Lys Leu Ser Cys Lys Ala Ser Gly Tyr Thr Phe Thr Ser Tyr
            20                  25                  30

Trp Met His Trp Val Lys Gln Arg Pro Gly Gln Gly Leu Glu Trp Ile
        35                  40                  45

Gly Leu Ile Asp Pro Ser Asp Ser Tyr Thr Asn Tyr Asn Gln Lys Phe
    50                  55                  60

Lys Gly Lys Ala Thr Leu Thr Val Asp Thr Ser Ser Ser Thr Ala Ser
65                  70                  75                  80

Met Gln Leu Ser Ser Leu Thr Ser Glu Asp Ser Ala Val Tyr Tyr Cys
                85                  90                  95

Val Arg Thr Tyr Tyr His Ser Ser Tyr Phe Phe Ala Tyr Trp Gly Gln
            100                 105                 110

Gly Thr Leu Val Thr Val Ser Ser Ala Lys Thr Thr Pro Pro Ser Val
        115                 120                 125

Tyr Pro
    130

<210> SEQ ID NO 17
<211> LENGTH: 330
<212> TYPE: DNA
<213> ORGANISM: Artificial Sequence
<220> FEATURE:
<223> OTHER INFORMATION: SYNTHESIZED

<400> SEQUENCE: 17

```
gacatccaga tgacccagtc tccagcctcc ctatctgcat ctgtgggaga aactgtcacc    60
atcacatgtc gaacaagtgg gaatattcac aattatttag catggtatca gcagaaacag   120
ggaaaatctc ctcagctcct ggtctataat gcaaaaacct tagcagatgg tgtgccatca   180
aggttcagtg gcagtggatc aggaacacaa tattctctca agatcaacag cctgcaacct   240
gaagattttg ggagttatta ctgtcaacat ttttggagta ttccattcac gttcggctcg   300
gggacaaagt tggaaataaa acgggctgat                                    330
```

<210> SEQ ID NO 18
<211> LENGTH: 390
<212> TYPE: DNA
<213> ORGANISM: Artificial Sequence
<220> FEATURE:
<223> OTHER INFORMATION: SYNTHESIZED

<400> SEQUENCE: 18

```
caggtccagc tgcagcagtc tggacctgag ctggtgaagc ctggggcttc agtgaagata    60
tcctgcaagg cttctggcta cagcttcaca agctactata tacactgggt gaagcagagg   120
cctggacagg gacttgagtg gattggatgg atttatcctg aagtggtaa ttctaagtac    180 aatgagaagt tcaagggcaa ggccacactg acggcagaca catcctccag tactgcctac   240
atgcaactca gcagcctaac atctgaggac tctgcggtct attactgtgc aagagacggt   300
agtacctaca actggaactt cgatgtctgg ggcacaggga ccacggtcac cgtctcctca   360
gccaaaacaa cacccccatc agtctatcca                                    390
```

<210> SEQ ID NO 19
<211> LENGTH: 333
<212> TYPE: DNA
<213> ORGANISM: Artificial Sequence
<220> FEATURE:
<223> OTHER INFORMATION: SYTHESIZED

<400> SEQUENCE: 19

```
gacattgtgg tgacacagtc tcctgcttcc tttgctgtat ctctggggca gagggccacc    60
atctcatgca gggccagcaa agtgtcagt acatctggct atagttatat aaactggtac    120
caacagaaac caggacagcc acccaaactg ctcatctatc ttgcatccaa cctagaatct   180
ggggtccctg ccaggttcag tggcagtggg tctgggacag acttcaccct caacatccat   240
cctgtggagg aggaggatgc tgcaacctat tactgtcagc acagtaggga gcttcctctc   300
acgttcggtg ctgggaccag gctggagctg aaa                                333
```

<210> SEQ ID NO 20
<211> LENGTH: 390
<212> TYPE: DNA
<213> ORGANISM: Artificial Sequence
<220> FEATURE:
<223> OTHER INFORMATION: SYNTHESIZED

<400> SEQUENCE: 20

```
caggtccaac tgcagcagcc tggggctgaa ctggtgaggc ctgggacttc agtgaaattg    60
tcctgcaagg cttctggcta caccttcacc agctactgga tgcactgggt aaacagagg   120 cctggacaag gccttgagtg gatcggtctg attgatcctt ctgatagtta tactaactac   180
aatcaaaagt tcaagggcaa ggccacattg actgtagaca catcctccag cacagcctcc   240
atgcaactca gcagcctgac atctgaggac tctgcggtct attactgtgt aagaacttac   300
```

```
taccatagta gctacttctt tgcttactgg ggccaaggga ctctggtcac tgtctcttca    360
gccaaaacaa cacccccatc agtctatcca                                    390
```

<210> SEQ ID NO 21
<211> LENGTH: 12
<212> TYPE: PRT
<213> ORGANISM: Homo sapiens

<400> SEQUENCE: 21

```
Arg Pro Tyr Tyr Gln Gly Leu Ile Asp Lys Tyr Cys
1               5                   10
```

<210> SEQ ID NO 22
<211> LENGTH: 13
<212> TYPE: PRT
<213> ORGANISM: Homo sapiens

<400> SEQUENCE: 22

```
Pro Ser Leu Val Tyr Arg Pro Asp Val Asp Pro Glu Val
1               5                   10
```

<210> SEQ ID NO 23
<211> LENGTH: 10
<212> TYPE: PRT
<213> ORGANISM: Homo sapiens

<400> SEQUENCE: 23

```
Gly Ser Pro Glu Phe Lys Val Thr Val Gly
1               5                   10
```

<210> SEQ ID NO 24
<211> LENGTH: 10
<212> TYPE: PRT
<213> ORGANISM: Schistosom a japonicum

<400> SEQUENCE: 24

```
Met Ser Pro Ile Leu Gly Tyr Trp Lys Ile
1               5                   10
```

<210> SEQ ID NO 25
<211> LENGTH: 29
<212> TYPE: PRT
<213> ORGANISM: Homo sapiens

<400> SEQUENCE: 25

```
Met Lys Val Thr Val Gly Pro Asp Pro Ser Leu Val Tyr Arg Pro Asp
1               5                   10                  15

Val Asp Pro Glu Val Ala Lys Asp Lys Ala Ser Phe Arg
            20                  25
```

<210> SEQ ID NO 26
<211> LENGTH: 16
<212> TYPE: PRT
<213> ORGANISM: Homo sapiens

<400> SEQUENCE: 26

```
Gly Leu Val Asp Glu Ser Asp Pro Asp Val Asp Phe Pro Asn Ser Phe
1               5                   10                  15
```

<210> SEQ ID NO 27
<211> LENGTH: 14
<212> TYPE: PRT
<213> ORGANISM: Homo sapiens

<400> SEQUENCE: 27

Asp Ser Thr Phe Gln Asp Asn Pro Asp Leu Gln Asp Pro Arg
1               5                   10

<210> SEQ ID NO 28
<211> LENGTH: 10
<212> TYPE: PRT
<213> ORGANISM: Homo sapiens

<400> SEQUENCE: 28

Gln Gly Leu Ile Asp Lys Tyr Cys Pro Gly
1               5                   10

<210> SEQ ID NO 29
<211> LENGTH: 284
<212> TYPE: PRT
<213> ORGANISM: Homo sapiens

<400> SEQUENCE: 29

Met Lys Val Thr Val Gly Pro Asp Pro Ser Leu Val Tyr Arg Pro Asp
1               5                   10                  15

Val Asp Pro Glu Val Ala Lys Asp Lys Ala Ser Phe Arg Asn Tyr Thr
            20                  25                  30

Ser Gly Pro Leu Leu Asp Arg Val Phe Thr Thr Tyr Lys Leu Met His
        35                  40                  45

Thr His Gln Thr Val Asp Phe Val Arg Ser Lys His Ala Gln Phe Gly
    50                  55                  60

Gly Phe Ser Tyr Lys Lys Met Thr Val Met Glu Ala Val Asp Leu Leu
65                  70                  75                  80

Asp Gly Leu Val Asp Glu Ser Asp Pro Asp Val Asp Phe Pro Asn Ser
                85                  90                  95

Phe His Ala Phe Gln Thr Ala Glu Gly Ile Arg Lys Ala His Pro Asp
            100                 105                 110

Lys Asp Trp Phe His Leu Val Gly Leu Leu His Asp Leu Gly Lys Val
        115                 120                 125

Leu Ala Leu Phe Gly Glu Pro Gln Trp Ala Trp Gly Asp Thr Phe Pro
    130                 135                 140

Val Gly Cys Arg Pro Gln Ala Ser Val Val Phe Cys Asp Ser Thr Phe
145                 150                 155                 160

Gln Asp Asn Pro Asp Leu Gln Asp Pro Arg Tyr Ser Thr Glu Leu Gly
                165                 170                 175

Met Tyr Gln Pro His Cys Gly Leu Asp Arg Val Leu Met Ser Trp Gly
            180                 185                 190

His Asp Glu Tyr Met Tyr Gln Val Met Lys Phe Asn Lys Phe Ser Leu
        195                 200                 205

Pro Pro Glu Ala Phe Tyr Met Ile Arg Phe His Ser Phe Tyr Pro Trp
    210                 215                 220

His Thr Gly Arg Asp Tyr Gln Gln Leu Cys Ser Gln Gln Asp Leu Ala
225                 230                 235                 240

Met Leu Pro Trp Val Arg Glu Phe Asn Lys Phe Asp Leu Tyr Thr Lys
                245                 250                 255

Cys Pro Asp Leu Pro Asp Val Asp Lys Leu Arg Pro Tyr Tyr Gln Gly
            260                 265                 270

Leu Ile Asp Lys Tyr Cys Pro Gly Ile Leu Ser Trp
        275                 280

-continued

```
<210> SEQ ID NO 30
<211> LENGTH: 13
<212> TYPE: PRT
<213> ORGANISM: Mus musculus

<400> SEQUENCE: 30

Pro Ser Leu Val Tyr Arg Pro Asp Val Asp Pro Glu Met
1               5                   10

<210> SEQ ID NO 31
<211> LENGTH: 13
<212> TYPE: PRT
<213> ORGANISM: Felis catus

<400> SEQUENCE: 31

Pro Ser Leu Val Tyr Arg Pro Asp Val Asp Pro Glu Ala
1               5                   10

<210> SEQ ID NO 32
<211> LENGTH: 13
<212> TYPE: PRT
<213> ORGANISM: Cavia porcellus

<400> SEQUENCE: 32

Pro Ser Leu Ile Tyr Arg Pro Asp Met Asp Pro Glu Met
1               5                   10

<210> SEQ ID NO 33
<211> LENGTH: 13
<212> TYPE: PRT
<213> ORGANISM: Spermophilus sensustricto

<400> SEQUENCE: 33

Pro Ser Leu Val Tyr Arg Pro Asp Val Gly Thr Glu Ala
1               5                   10

<210> SEQ ID NO 34
<211> LENGTH: 13
<212> TYPE: PRT
<213> ORGANISM: Canis canis

<400> SEQUENCE: 34

Pro Ser Leu Val Tyr Arg Pro Asp Met Asp Pro Glu Lys
1               5                   10
```

MIOX ANTIBODY AND ASSAY

CROSS REFERENCE TO RELATED APPLICATIONS

This application claims the benefit of PCT Application PCT/US2014/046383, filed Jul. 11, 2014, which claims the benefit of U.S. provisional application No. 61/845,108, filed Jul. 11, 2013, each of the disclosures of which are hereby incorporated by reference in its entirety.

GOVERNMENT SUPPORT

This invention was made with government support under P30 DK0793305 awarded by the NIH. The government has certain rights in the invention.

FIELD OF THE INVENTION

The invention relates to compositions and methods for detecting renal injury in a subject, such as proximal tubular injury associated with acute kidney injury.

REFERENCE TO SEQUENCE LISTING

A paper copy of the sequence listing and a computer readable form of the same sequence listing are appended below and herein incorporated by reference. The information recorded in computer readable form is identical to the written sequence listing, according to 37 C.F.R. 1.821(f).

BACKGROUND OF THE INVENTION

Acute kidney injury is common amongst hospitalized and critically ill patients and its incidence is increasing. Approximately 45% of critically ill patients and 20% of hospitalized patients develop acute kidney injury (Li P K et al. Kidney Int. 2013; 83:372; Bellomo R, et al. Lancet 2012; 380:756-766; Goldstein S L Blood Purif. 2012; 33:131-137). The result is increased hospital stays, infectious complications and increased mortality at significant cost (Nash H et al. Am J Kidney Dis. 2002; 39:930; Liangos O et al. Clin J Am Soc Nephrol. 2006; 1:43; Xue J L et al. J Am Soc Nephrol 2006; 17:1135; Palevsky P M N Engl J Med. 2009; 361:1699; Himmelfarb J and Ikizler T A Kidney Int 2007; 71:971; Schrier R W et al. J Clin Invest. 2004; 114:5; Singbartl K et al. Kidney Int 2012; 81:819-825). Recent studies have also linked episodes of acute kidney injury with future development of chronic kidney disease (Coca S G et al. Kidney Int. 2012; 81:442; Bydash J R et al. Clin J Am Soc Nephrol. 2011; 6:2555). Multiple factors contribute to the development of acute kidney injury including sepsis, ischemia, drugs, intravenous contrast, and infection (Star R A Kidney Int 1998; 54:1817; Thadhani R et al. N Engl J Med 1996; 334:1448; Perazella M A Kidney Int. 2012; 81:1172-1178; Zarjou A and Agarwal A J Am Soc Nephrol. 2011; 22:999; Solomon R and Dauerman H L Circulation 2010; 122:2451; Collins A J et al. Am J Kidney Dis. 2011; 57(1)(suppl 1):e1-e526).

The current standard for identifying acute kidney injury, serum creatinine, is non-specific and insensitive (Waikar S S, et al. 2009; 24:3263; Bolignano D. Clin Chem Lab Med 2012; 50:1495; Star R A. Kidney Int. 1998; 54:1817). Serum creatinine may not increase until days after the injury has occurred or until 50% of renal function has been lost, precluding effective treatment. Additionally, conditions other than kidney injury may cause elevations in serum creatinine. Moreover, serum creatinine is unable to accurately predict glomerular filtration rate (GFR) in the non-steady state of acute kidney injury, underestimating the decline in renal function. Lastly, since serum creatinine depends on muscle mass and hepatic function, serum concentrations may differ depending on the patient's muscle content and liver function (Waikar S S, et al. Nephrol Dial Transplant 2009; 24:3263; Bolignano D. Clin Chem Lab Med 2012; 50:1495; Star R A. Kidney Int. 1998; 54:1817).

There is a critical unmet need for a real-time, specific, and sensitive biomarker of acute kidney injury. The American Society of Nephrology, Acute Dialysis Quality Initiative, and Acute Kidney Injury Network have all prioritized the identification and validation of acute kidney injury biomarkers (Kellum J A et al. Clin J Am Soc Nephrol. 2008; 3:887; Mehta R L et al. Crit Care 2007; 11:R31). Early detection of acute kidney injury may allow for timely intervention and perhaps decrease its significant morbidity and mortality (Schrier R W J Am Soc Nephrol 2004; 15:2756). Although multiple new drugs have been developed to treat acute kidney injury, they have not proven effective in a clinical setting (Noguchi S, et al. J Pharmacol Exp Ther 1993; 267:919-26; Conger J D, et al. Kidney Int 1989; 35:1126-32; Allgren R L, et al. N Engl J Med. 1997; 336:828-34; Tumlin J A, et al. Am J Kidney Dis 2005; 46:26-34; Hirschberg R, et al. Kidney Int. 1999; 55:2423-32; Denton M D, et al. Kidney Int. 1996; 50:4-14; Acker C G et al. Kidney Int. 2000; 57:293-8). This has been attributed, at least partially, to the inability to detect kidney injury early. Multiple studies have investigated a variety of plasma and urine biomarkers for the diagnosis of acute kidney injury (Kashani K et al. Crit Care 2013; 17:R25; Siew E D et al. J Am Soc Nephrol. 2011; 22:810; Dieterle F, et al. Nat Biotechnol. 2010; 28:455; Devarajan P Nephrology (Carlton) 2010 15:419; Waikar S S and Bonventre J V Nephron Clin Pract 2008; 109:c192). Although significant progress has been made, no specific, early biomarkers of acute kidney injury have translated into clinical practice.

SUMMARY OF THE INVENTION

In an aspect, the present disclosure encompasses an isolated antibody. The antibody specifically binds MIOX and recognizes an epitope within an amino acid sequence selected from the group consisting of SEQ ID NO: 21 and SEQ ID NO:22.

In another aspect, the present disclosure encompasses an isolated antibody. The antibody specifically binds MIOX and comprises a heavy chain CDR3 comprising the amino acid sequence of SEQ ID NO: 6 with zero to two amino acid substitutions.

In still another aspect, the present disclosure encompasses an isolated antibody. The antibody specifically binds MIOX and comprises a heavy chain CDR3 comprising the amino acid sequence of SEQ ID NO: 12 with zero to two amino acid substitutions.

In still yet another aspect, the present disclosure encompasses an isolated antibody. The antibody specifically binds MIOX and comprises a light chain CDR3 comprising the amino acid sequence of SEQ ID NO: 3 with zero to two amino acid substitutions.

In still another embodiment, the present disclosure encompasses an isolated antibody. The antibody specifically binds MIOX and comprises a light chain CDR3 comprising the amino acid sequence of SEQ ID NO: 9 with zero to two amino acid substitutions.

In still yet another embodiment, the present disclosure encompasses a method for measuring the amount of MIOX in a biological sample. The method comprises (i) obtaining a sample of biological fluid from a subject; and (ii) measuring the amount of MIOX in the sample by immunoassay comprising at least one isolated antibody that specifically binds MIOX. The antibody comprises an amino acid sequence selected from the group consisting of SEQ ID NO: 1-12 with zero to two amino acid substitutions.

In yet still another aspect, the present disclosure encompasses a method for detecting renal injury in a subject. The method comprises (i) obtaining a biological sample from a subject; (ii) measuring the amount of MIOX in the sample by immunoassay using at least one isolated antibody that specifically binds MIOX, wherein the antibody comprises an amino acid sequence selected from the group consisting of SEQ ID NO: 1-12 with zero to two amino acid substitutions; and (iii) comparing the amount of MIOX in the sample to a reference value. A greater amount of MIOX in the sample compared to the reference value indicates renal injury in the subject.

In another aspect, the present disclosure encompasses a method for detecting proximal tubular injury in a subject. The method comprises (i) obtaining a sample of biological fluid from a subject; (ii) measuring the amount of MIOX in the sample by immunoassay using at least one isolated antibody that specifically binds MIOX, wherein the antibody comprises an amino acid sequence selected from the group consisting of SEQ ID NO: 1-12 with zero to two amino acid substitutions; and (iii) comparing the amount of MIOX in the sample to a reference value. A greater amount of MIOX in the sample compared to the reference value indicates proximal tubular injury in the subject.

BRIEF DESCRIPTION OF THE FIGURES

The application file contains at least one drawing executed in color. Copies of this patent application publication with color drawing(s) will be provided by the Office upon request and payment of the necessary fee.

(FIG. 1A) MIOX mRNA expression profile in mouse tissues. Bars represent MIOX microarray units (y-axis) for each tissue sample (x-axis). Samples were obtained and analyzed as described previously (Clin Chem (2006) 52, 1713-1721). (FIG. 1B) Examination of MIOX expression in human tissue homogenates using a rabbit polyclonal anti-MIOX antibody. The pre-made blot (TB37-set I, GBiosciences, Saint Louis, Mo.) was immunostained with R9544 and detected with goat-anti-rabbit-alkaline phosphatase.

(FIG. 2A) This low-power view demonstrates intense staining within the renal cortex (40×). (FIG. 2B) On high power examination, the proximal tubules show strong MIOX immunoreactivity. In contrast, the adjacent distal tubules, glomeruli, and blood vessels show no significant immunoreactivity (400×).

FIG. 3A, FIG. 3B, FIG. 3C, FIG. 3D and FIG. 3E depict images of Western blots confirming the specificity of the anti-MIOX antibodies and images of immunoblots showing characterization of the linear epitopes for mAb 01D10 and mAb 12H06. (FIG. 3A) Western blot of 10 µg normal human kidney homogenate (kidney) with the rabbit anti-MIOX polyclonal antibody and the mouse monoclonal antibodies 12H06 and 01D10. Recombinant GST-MIOX (rMIOX, 10 µg) was cut with thrombin, run on the same gel, transferred to polyvinylidene difluoride, and protein stained. The protein-stained bands were subjected to Edman sequencing and confirmed to represent MIOX and GST as indicated. The remaining lanes were cut and stained with the rabbit polyclonal anti-MIOX antibody (pAb R9544), mouse monoclonal anti-MIOX antibody 12H06 (mAb 12H06), and mouse monoclonal antibody 01D10 (mAb 01D10). Nonspecific bands were identified by use of pAb R9544 (~64 and ~22 kDa) and the mAb 12H06 (~40 kDa). The only band that reacted with all 3 antibodies corresponded to recombinant MIOX (~33 kDa). (FIG. 3B) Identification of anti-MIOX antibody epitopes. Spot-peptide membrane array immunostaining for rabbit polyclonal antibody R9544, mouse monoclonal antibody 01D10 (mAb 01D10), and mouse monoclonal antibody 12H06 (mAb 12H06). Each spot comprised a 10-mer synthetic peptide: spot 1, residues 1-10; spot 2, residues 3-12; spot 3, residues 5-14 (and so on) until the entire sequence was covered. The numbers to the left of the blots correspond to the spot number at the beginning of the row. *End of the sequence. (FIG. 3C), Representation of anti-MIOX antibody epitopes. The amino acid sequence of MIOX is shown (SEQ ID NO:29; AA 1-285). The epitope map of the rabbit polyclonal anti-MIOX antibody is italicized (SEQ ID NO:25 (AA 1-29), SEQ ID NO:26 (AA 82-97), SEQ ID NO:27 (AA 158-171), SEQ ID NO:28 (AA 272-281), mouse monoclonal antibody 12H06 is bold and underlined (SEQ ID NO:21; AA 268-279), and the mouse monoclonal antibody 01D10 is boxed (SEQ ID NO:22; AA 9-21). The mAb 01D10 antibody recognizes an epitope near the N-terminus, and the mAb 12H06 antibody recognizes an epitope near the C-terminus. The polyclonal antibody reacts with N- and C-terminal epitopes and 2 internal epitopes. (FIG. 3D) Western blot of normal kidney homogenate from human (H), mouse (M), and rat (R) (G-Biosciences, St. Louis, Mo.) using the 01D10 mouse monoclonal antibody. Samples were loaded at 50 µg/lane. (FIG. 3E) Western blot of human, mouse, and rat kidney homogenate using the 12H06 mouse monoclonal antibody.

(FIG. 4A) The peptides corresponding to the epitopes for mAb 01D10 (peptide 1) and mAb 12H06 (peptide 2) were synthesized. mAb 01D10 was pre-incubated for one hour with buffer alone, 100 µg/ml peptide 1, or 100 µg/ml peptide 2. (FIG. 4B) Western inhibition of mAb 12H06 using either peptide 1 or peptide 2.

(FIG. 5A) Miox was measured in mouse serum from sham-operated animals, animals at baseline, and 24 hours after AKI (n=5). Miox was below the limit of detection (LOD) [115 (55) pg/mL] in sham-operated animals and at baseline. Serum Miox was increased 24 h post-injury [2.8 (0.7) ng/mL, mean (SE); *P<0.03]. (FIG. 5B) Representative section of renal cortex from a sham-operated mouse shows intact renal tubules (H&E, 400×). (FIG. 5C) Representative section of renal cortex 24 h postinjury. Extensive tubular necrosis is evident (arrows) (H&E, 400×). (FIG. 5D) Blood urea nitrogen levels at baseline and 24 hours after ischemia-repurfusion injury (IRI).

(FIG. 6A) CT scan from a patient with acute kidney injury. The right kidney shows poor perfusion, consistent with ischemia. (FIG. 6B) Serum creatinine was obtained at the time of presentation to the emergency room and 33 hours later. No prior creatinine values were available for comparison. (FIG. 6C) Plasma MIOX was markedly elevated at the time of presentation. Plasma MIOX decreased, but remained detectable, 33 hours later.

(FIG. 7A) Plasma creatinine (Cr) peaked 54.3 (3.8) h (time 54) relative to the preceding Cr measurement (time 0) and was increased at time 54 in patients with AKI (**P<0.005). (FIG. 7B) Patients with AKI showed higher plasma MIOX concentrations at time 0 and time 54 compared with patients without AKI (*P=0.002). To convert creatinine in mg/dL to mmol/L, multiply by 0.0884.

(FIG. 8A) Plasma creatinine is similar among all groups at time 0. (FIG. 8B) Plasma MIOX increased at time 0 in patients with oliguric and dialysis-requiring AKI. (FIG. 8C) Plasma creatinine increased at time 54 in patients with AKI. (FIG. 8D) Plasma MIOX was increased at time 54 in patients with oliguric and dialysis-requiring AKI relative to patients without AKI. *P<0.05. To convert creatinine in mg/dL to mmol/L, multiply by 0.0884.

(FIG. 9A) Patient 001 with AKI, Stage 2; (FIG. 9B) Patient 002 with no AKI; (FIG. 9C) Patient 003 with AKI, Stage 3; and (FIG. 9D) Patient 004 with AKI, Stage 1.

(FIG. 10A) Patient 001 with AKI, Stage 2; (FIG. 10B) Patient 002 with no AKI; (FIG. 10C) Patient 003 with AKI, Stage 3; and (FIG. 10D) Patient 004 with AKI, Stage 1.

DETAILED DESCRIPTION

Figure 1A:
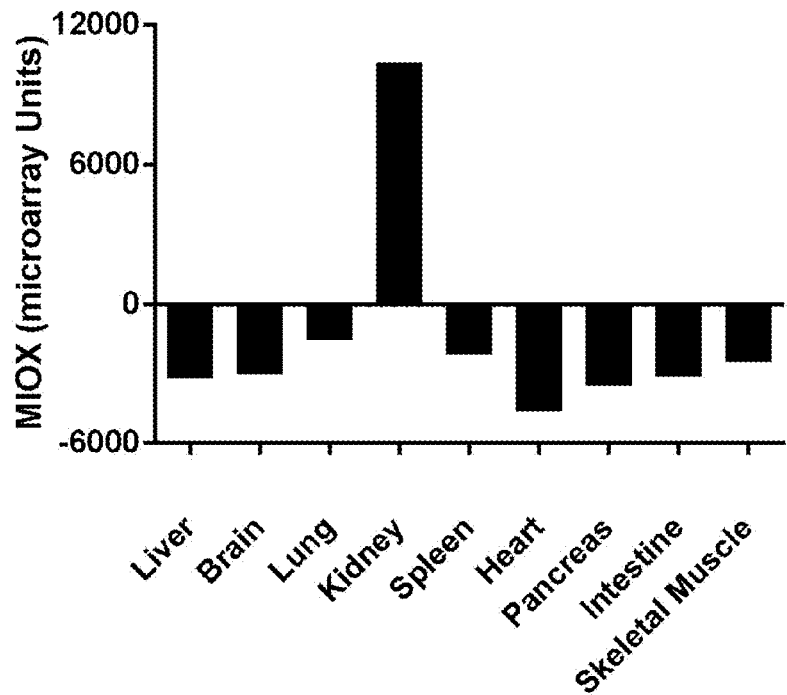
FIG. 1A and FIG. 1B depict a bar graph and image showing MIOX gene expression and MIOX protein are kidney-specific.

Applicants have discovered antibodies and methods of use thereof for detecting renal injury in a subject. The method comprises detecting and measuring the amount of myo-inositol oxygenase (MIOX) in a biological sample obtained from a subject using an anti-MIOX antibody. The present invention encompasses the discovery that MIOX is a kidney specific protein that is abundantly expressed in the proximal tubule, and it is detectable in biological fluids earlier than existing biomarkers of acute kidney injury. Thus, the invention provides evidence that detection of increased MIOX in a biological fluid following kidney injury is likely directly related to protein loss from the cells of the proximal tubule. In an aspect, an increased amount of MIOX in a biological fluid indicates proximal tubular cell damage. In another aspect, an increased amount of MIOX in a biological fluid indicates loss of MIOX from the proximal renal tubule. In still another aspect, an increased amount of MIOX in a biological fluid indicates proximal tubule injury. In still yet another aspect, an increased amount of MIOX in a biological fluid indicates renal injury associated with proximal tubule injury. In yet still another aspect, antibodies useful in detecting an increased amount of MIOX in a biological fluid include those which bind an epitope within MIOX.

I. Anti-MIOX Antibodies

Anti-MIOX antibodies useful herein include all antibodies that specifically bind an epitope within MIOX. Generally speaking, the epitope is detectable following proximal tubular cell damage. The epitope may or may not be detectable in the absence of proximal tubular cell damage. For example, proximal tubular cell damage may modify the protein such that a previously undetectable epitope becomes detectable. Alternatively, an epitope may be detectable both in the in the absence of proximal tubular cell damage and following proximal tubular cell damage, though the detectable signal is greater following proximal tubular cell damage. Anti-MIOX antibodies useful herein also include antibodies that bind to specific regions of MIOX and to other forms of MIOX. Specific regions of MIOX include, but are not limited to, the C-terminal, the N-terminal, and other central domains. Other forms of MIOX include but are not limited to truncated, modified, soluble, insoluble, intracellular, extracellular, and dimerized or otherwise oligomerized forms, as well as MIOX complexed with other proteins or molecules.

Anti-MIOX antibodies useful herein include those which are isolated, characterized, purified, functional and have been recovered (obtained) from a process for their preparation and thus available for use herein in a useful form in an amount sufficient for an assay to detect and measure the amount of MIOX in a biological sample.

The term "antibody" includes the term "monoclonal antibody". "Monoclonal antibody" refers to an antibody that is derived from a single copy or clone, including e.g., any eukaryotic, prokaryotic, or phage clone. "Monoclonal antibody" is not limited to antibodies produced through hybridoma technology. Monoclonal antibodies can be produced using e.g., hybridoma techniques well known in the art, as well as recombinant technologies, phage display technologies, synthetic technologies or combinations of such technologies and other technologies readily known in the art. Furthermore, the monoclonal antibody may be labeled with a detectable label, immobilized on a solid phase and/or conjugated with a heterologous compound (e.g., an enzyme or toxin) according to methods known in the art.

Further by "antibody" is meant a functional monoclonal antibody, or an immunologically effective fragment thereof; such as an Fab, Fab', or F(ab')2 fragment thereof. In some contexts herein, fragments will be mentioned specifically for emphasis; nevertheless, it will be understood that regardless of whether fragments are specified, the term "antibody" includes such fragments as well as single-chain forms. As long as the protein retains the ability specifically to bind its intended target, it is included within the term "antibody." Also included within the definition "antibody" for example are single chain forms, generally designated Fv, regions, of antibodies with this specificity.

Preferably, but not necessarily, the antibodies useful in the discovery are produced recombinantly, as manipulation of the typically murine or other non-human antibodies with the appropriate specificity is required in order to convert them to humanized form. Antibodies may or may not be glycosylated, though glycosylated antibodies are preferred. Antibodies are properly cross-linked via disulfide bonds, as is known.

The basic antibody structural unit of an antibody useful herein comprises a tetramer. Each tetramer is composed of two identical pairs of polypeptide chains, each pair having one "light" (about 25 kDa) and one "heavy" chain (about 50-70 kDa). The amino-terminal portion of each chain includes a variable region of about 100 to 110 or more amino acid sequences primarily responsible for antigen recognition. The carboxy-terminal portion of each chain defines a constant region primarily responsible for effector function.

Light chains are classified as gamma, mu, alpha, and lambda. Heavy chains are classified as gamma, mu, alpha, delta, or epsilon, and define the antibody's isotype as IgG, IgM, IgA, IgD and IgE, respectively. Within light and heavy chains, the variable and constant regions are joined by a "J" region of about 12 or more amino acid sequences, with the heavy chain also including a "D" region of about 10 more amino acid sequences.

The variable regions of each light/heavy chain pair form the antibody binding site. Thus, an intact antibody has two binding sites. The chains exhibit the same general structure of relatively conserved framework regions (FR) joined by three hypervariable regions, also called complementarity determining regions (hereinafter referred to as "CDRs.") The CDRs from the two chains are aligned by the framework regions, enabling binding to a specific epitope. From N-terminal to C-terminal, both light and heavy chains comprise the domains FR1, CDR1, FR2, CDR2, FR3, CDR3 and FR4 respectively. The assignment of amino acid sequences to each domain is in accordance with known conventions (See, Kabat "Sequences of Proteins of Immunological Interest" National Institutes of Health, Bethesda, Md., 1987 and 1991; Chothia, et al, J. Mol. Bio. (1987) 196:901-917; Chothia, et al., Nature (1989) 342:878-883).

In an aspect, monoclonal anti-MIOX antibodies are generated with appropriate specificity by standard techniques of immunization of mammals, forming hybridomas from the antibody-producing cells of said mammals or otherwise immortalizing them, and culturing the hybridomas or immortalized cells to assess them for the appropriate specificity. In the present case, such antibodies could be generated by immunizing a human, rabbit, rat or mouse, for example, with a peptide representing an epitope encompassing a region of the MIOX protein coding sequence or an appropriate subregion thereof. Materials for recombinant manipulation can be obtained by retrieving the nucleotide sequences encoding the desired antibody from the hybridoma or other cell that produces it. These nucleotide sequences can then be manipulated and isolated, characterized, purified and, recovered to provide them in humanized form, for use herein if desired.

As used herein "humanized antibody" includes an anti-MIOX antibody that is composed partially or fully of amino acid sequence sequences derived from a human antibody germline by altering the sequence of an antibody having non-human complementarity determining regions ("CDR"). The simplest such alteration may consist simply of substituting the constant region of a human antibody for the murine constant region, thus resulting in a human/murine chimera which may have sufficiently low immunogenicity to be acceptable for pharmaceutical use. Preferably, however, the variable region of the antibody and even the CDR is also humanized by techniques that are by now well known in the art. The framework regions of the variable regions are substituted by the corresponding human framework regions leaving the non-human CDR substantially intact, or even replacing the CDR with sequences derived from a human genome. CDRs may also be randomly mutated such that binding activity and affinity for MIOX is maintained or enhanced in the context of fully human germline framework regions or framework regions that are substantially human. Substantially human frameworks have at least 90%, 95%, or 99% sequence identity with a known human framework sequence. Fully useful human antibodies are produced in genetically modified mice whose immune systems have been altered to correspond to human immune systems. As mentioned above, it is sufficient for use in the methods of this discovery, to employ an immunologically specific fragment of the antibody, including fragments representing single chain forms.

Further, as used herein the term "humanized antibody" refers to an anti-MIOX antibody comprising a human framework, at least one CDR from a nonhuman antibody, and in which any constant region present is substantially identical to a human immunoglobulin constant region, i.e., at least about 85-90%, preferably at least 95% identical. Hence, all parts of a humanized antibody, except possibly the CDRs, are substantially identical to corresponding pairs of one or more native human immunoglobulin sequences.

If desired, the design of humanized immunoglobulins may be carried out as follows. When an amino acid sequence falls under the following category, the framework amino acid sequence of a human immunoglobulin to be used (acceptor immunoglobulin) is replaced by a framework amino acid sequence from a CDR-providing nonhuman immunoglobulin (donor immunoglobulin): (a) the amino acid sequence in the human framework region of the acceptor immunoglobulin is unusual for human immunoglobulin at that position, whereas the corresponding amino acid sequence in the donor immunoglobulin is typical for human immunoglobulin at that position; (b) the position of the amino acid sequence is immediately adjacent to one of the CDRs; or (c) any side chain atom of a framework amino acid sequence is within about 5-6 angstroms (center-to-center) of any atom of a CDR amino acid sequence in a three dimensional immunoglobulin model (Queen, et al., op. cit., and Co, et al, Proc. Natl. Acad. Sci. USA (1991) 88:2869). When each of the amino acid sequences in the human framework region of the acceptor immunoglobulin and a corresponding amino acid sequence in the donor immunoglobulin is unusual for human immunoglobulin at that position, such an amino acid sequence is replaced by an amino acid sequence typical for human immunoglobulin at that position.

In all instances, an antibody of the invention specifically binds MIOX. In exemplary embodiments, an antibody of the invention specifically binds human MIOX. The phrase "specifically binds" herein means antibodies bind to the protein with an affinity constant or Affinity of interaction ($K_D$) in the range of at least 0.1 mM to 1 pM, or in the range of at least 0.1 pM to 10 nM, with a preferred range being 0.1 pM to 1 nM. The sequence of MIOX from a variety of species is known in the art, and methods of determining whether an antibody binds to MIOX are known in the art. For instance, see the Examples.

The antibodies of the present invention may also be used as fusion proteins known as single chain variable fragments (scFv). These scFvs are comprised of the heavy and light chain variable regions connected by a linker. In most instances, but not all, the linker may be a peptide. A linker peptide is preferably from about 10 to 25 amino acids in length. Preferably, a linker peptide is rich in glycine, as well as serine or threonine. ScFvs can be used to facilitate phage display or can be used for flow cytometry, immunohistochemistry, or as targeting domains. Methods of making and using scFvs are known in the art.

In a preferred embodiment, the scFvs of the present invention are conjugated to a human constant domain. In some embodiments, the heavy constant domain is derived from an IgG domain, such as IgG1, IgG2, IgG3, or IgG4. In other embodiments, the heavy chain constant domain may be derived from IgA, IgM, or IgE.

An isolated antibody of the present invention that binds to MIOX preferably recognizes one of several epitopes. In one embodiment, the isolated antibody of the present invention that binds to MIOX recognizes an epitope within the amino acid sequences of SEQ ID NO: 21 (RPYYQGLIDKYC). Preferably, the isolated antibody recognizes an epitope within at least three contiguous amino acids of SEQ ID NO: 21, including within at least 4 contiguous amino acids of SEQ ID NO: 21, within at least 5 contiguous amino acids of SEQ ID NO: 21, within at least 6 contiguous amino acids of SEQ ID NO: 21, within at least 7 contiguous amino acids of SEQ ID NO: 21, within at least 8 contiguous amino acids of SEQ ID NO: 21, within at least 9 contiguous amino acids of SEQ ID NO: 21, within at least 10 contiguous amino acids of SEQ ID NO: 21, within at least 11 contiguous amino acids of SEQ ID NO: 21, and within at least 12 contiguous amino acids of SEQ ID NO: 21. In an exemplary embodiment, an isolated antibody of the present invention that recognizes an epitope within SEQ ID NO: 21 is the antibody 12H06.

In another embodiment, the isolated antibody of the present invention that binds to MIOX recognizes an epitope within the amino acid sequence of SEQ ID NO: 22 (PSLVYRPDVDPEV). Preferably, the isolated antibody recognizes an epitope within at least three contiguous amino acids of SEQ ID NO: 22, including within at least 4 contiguous amino acids of SEQ ID NO: 22, within at least 5 contiguous amino acids of SEQ ID NO: 22, within at least 6 contiguous amino acids of SEQ ID NO: 22, within at least 7 contiguous amino acids of SEQ ID NO: 22, within at least 8 contiguous amino acids of SEQ ID NO: 22, within at least 9 contiguous amino acids of SEQ ID NO: 22, within at least 10 contiguous amino acids of SEQ ID NO: 22, within at least 11 contiguous amino acids of SEQ ID NO: 22, and within at least 12 contiguous amino acids of SEQ ID NO: 22, and within at least 13 contiguous amino acids of SEQ ID NO:22. In an exemplary embodiment, an isolated antibody of the present invention that recognizes an epitope within SEQ ID NO: 22 is the antibody 01D10.

The human MIOX protein shows 89.8%, 90.5%, 89.2%, 89.8%, 89.1%, 92.3%, and 88.8% homology with mouse, rat, pig, guinea pig, ground squirrel, cat, and dog MIOX, respectively. The antibody epitope sequence of the human and various animal epitopes show significant homology (Table A). In one embodiment, an antibody of the invention may recognize human MIOX. In another embodiment, an antibody of the invention may recognize rat MIOX. In another embodiment, an antibody of the invention may recognize mouse MIOX. In another embodiment, an antibody of the invention may recognize cat MIOX. In another embodiment, an antibody of the invention may recognize dog MIOX. In another embodiment, an antibody of the invention may recognize pig MIOX. Antibodies of the invention may also bind MIOX from other species.

TABLE A

MIOX epitope sequence similarity between human MIOX and other species

| SEQ ID NO: | 12H06 epitope | Species | 01D10 epitope | SEQ ID NO: |
|---|---|---|---|---|
| 21 | RPYYQGLIDKYC | Human | PSLVYRPDVDPEV | 22 |
| 21 | RPYYQGLIDKYC | Mouse | PSLVYRPDVDPEM | 30 |
| 21 | RPYYQGLIDKYC | Rat | PSLVYRPDVDPEM | 30 |
| 21 | RPYYQGLIDKYC | Pig | PSLVYRPDVDPEA | 31 |
| 21 | RPYYQALIDKYC | Guinea Pig | PSLIYRPDMDPEM | 32 |
| 21 | RPYYQELIDKYC | Ground Squirrel | PSLVYRPDVGTEA | 33 |
| 21 | RPYYQGLIDKYC | Cat | PSLVYRPDVDPEA | 31 |
| 21 | RPYYQGLIDKYC | Dog | PSLVYRPDMDPEK | 34 |

A preferred antibody is a mouse antibody derived from a hybridoma designated 01D10 or 12H06 (Gaut J P, et al. Clin Chem. 2014:60(5):747-57). As used herein, the term "derived from" means that the "derived" antibody comprises at least one CDR region from the antibody produced by 01D10 or 12H06. Stated another way, the "derived antibody" comprises at least one CDR region comprised of the amino acid sequence selected from the group consisting of SEQ ID NO: 1, 2, 3, 4, 5, 6, 7, 8, 9, 10, 11, and 12.

In one embodiment, an antibody of the invention may be derived from the hybridoma 01D10, and may be encoded by a nucleic acid sequence comprising 90, 91, 92, 93, 94, 95, 96, 97, 98, or 99% identity to the light chain variable region of SEQ ID NO:17, or may be encoded by a nucleic acid sequence comprising 90, 91, 92, 93, 94, 95, 96, 97, 98, or 99% identity to the heavy chain variable region of SEQ ID NO:18. In another embodiment, an antibody of the invention may be derived from the hybridoma 01D10, and may be encoded by an amino acid sequence comprising 90, 91, 92, 93, 94, 95, 96, 97, 98, or 99% identity to the light chain variable region of SEQ ID NO:13, or may be encoded by a nucleic acid sequence comprising 90, 91, 92, 93, 94, 95, 96, 97, 98, or 99% identity to the heavy chain variable region of SEQ ID NO:14. In each of the above embodiments, the antibody may be humanized.

In a different embodiment, an antibody of the invention may be derived from the hybridoma 12H06, and may be encoded by a nucleic acid sequence comprising 90, 91, 92, 93, 94, 95, 96, 97, 98, or 99% identity to the light chain variable region of SEQ ID NO:19, or may be encoded by a nucleic acid sequence comprising 90, 91, 92, 93, 94, 95, 96, 97, 98, or 99% identity to the heavy chain variable region of SEQ ID NO:20. In another embodiment, an antibody of the invention may be derived from the hybridoma 12H06, and may be encoded by an amino acid sequence comprising 90, 91, 92, 93, 94, 95, 96, 97, 98, or 99% identity to the light chain variable region of SEQ ID NO:15, or may be encoded by an amino acid sequence comprising 90, 91, 92, 93, 94, 95, 96, 97, 98, or 99% identity to the heavy chain variable region of SEQ ID NO:16. In each of the above embodiments, the antibody may be humanized.

In an exemplary embodiment of an antibody of the invention that binds to MIOX, the antibody comprises the light chain amino acid sequence of SEQ ID NO:13 and the heavy chain amino acid sequence of SEQ ID NO:14 [i.e. the monoclonal antibody referred to herein as mAb 01D10]. In another exemplary embodiment of an antibody of the invention that binds to MIOX, the antibody comprises the light chain amino acid sequence of SEQ ID NO:15 and the heavy chain amino acid sequence of SEQ ID NO:16 [i.e. the monoclonal antibody referred to herein as mAb 12H06]. In another exemplary embodiment of an antibody of the invention that binds to MIOX, the antibody comprises the light chain nucleic acid sequence of SEQ ID NO:17 and the heavy chain amino acid sequence of SEQ ID NO:18 [i.e. the monoclonal antibody referred to herein as mAb 01D10]. In another exemplary embodiment of an antibody of the invention that binds to MIOX, the antibody comprises the light chain nucleic acid sequence of SEQ ID NO:19 and the heavy chain nucleic acid sequence of SEQ ID NO:20 [i.e. the monoclonal antibody referred to herein as mAb 12H06]. In each of the above embodiments, the antibody may be humanized.

In one embodiment, an antibody of the invention may comprise a light chain CDR1, such as the antibodies 1 and 49 of Table B. In another embodiment, an antibody of the invention may comprise a light chain CDR2, such as the antibodies 4 and 52 of Table B. In yet another embodiment, an antibody of the invention may comprise a light chain CDR3, such as the antibodies 6 and 54 of Table B. In an alternative embodiment, an antibody of the invention may comprise a combination of two or three light chain CDRs, such as the antibodies 2, 3, 5, 50, 51, and 53 of Table B. In each of the above embodiments, the antibody may be humanized.

Similarly, in one embodiment, an antibody of the invention may comprise a heavy chain CDR1, such as the antibodies 7 and 55 of Table B. In another embodiment, an antibody of the invention may comprise a heavy chain CDR2, such as the antibodies 10 and 58 of Table B. In yet another embodiment, an antibody of the invention may comprise a heavy chain CDR3, such as the antibodies 12 and 60 of Table B. In an alternative embodiment, an antibody of the invention may comprise a combination of two or three heavy chain CDRs, such as the antibodies 8, 9, 11, 56, 57, and 59 of Table B. In each of the above embodiments, the antibody may be humanized.

Alternatively, an antibody of the invention may comprise one or more light chain CDRs and one or more heavy chain CDRs, such as the antibodies 13-48, and 61-96 of Table B. In each of the above embodiments, the antibody may be humanized.

TABLE B

|  | Light Chain | | | Heavy Chain | | |
| --- | --- | --- | --- | --- | --- | --- |
| Antibody | CDR1 | CDR2 | CDR3 | CDR1 | CDR2 | CDR3 |
| 1 | SEQ ID NO: 1 | | | | | |
| 2 | SEQ ID NO: 1 | SEQ ID NO: 2 | | | | |
| 3 | SEQ ID NO: 1 | SEQ ID NO: 2 | SEQ ID NO: 3 | | | |
| 4 | | SEQ ID NO: 2 | | | | |
| 5 | | SEQ ID NO: 2 | SEQ ID NO: 3 | | | |
| 6 | | | SEQ ID NO: 3 | | | |
| 7 | | | | SEQ ID NO: 4 | | |
| 8 | | | | SEQ ID NO: 4 | SEQ ID NO: 5 | |
| 9 | | | | SEQ ID NO: 4 | SEQ ID NO: 5 | SEQ ID NO: 6 |
| 10 | | | | | SEQ ID NO: 5 | |
| 11 | | | | | SEQ ID NO: 5 | SEQ ID NO: 6 |
| 12 | | | | | | SEQ ID NO: 6 |
| 13 | SEQ ID NO: 1 | | | SEQ ID NO: 4 | | |
| 14 | SEQ ID NO: 1 | | | SEQ ID NO: 4 | SEQ ID NO: 5 | |
| 15 | SEQ ID NO: 1 | | | SEQ ID NO: 4 | SEQ ID NO: 5 | SEQ ID NO: 6 |
| 16 | SEQ ID NO: 1 | | | | SEQ ID NO: 5 | |
| 17 | SEQ ID NO: 1 | | | | SEQ ID NO: 5 | SEQ ID NO: 6 |
| 18 | SEQ ID NO: 1 | | | | | SEQ ID NO: 6 |
| 19 | SEQ ID NO: 1 | SEQ ID NO: 2 | | SEQ ID NO: 4 | | |
| 20 | SEQ ID NO: 1 | SEQ ID NO: 2 | | SEQ ID NO: 4 | SEQ ID NO: 5 | |
| 21 | SEQ ID NO: 1 | SEQ ID NO: 2 | | SEQ ID NO: 4 | SEQ ID NO: 5 | SEQ ID NO: 6 |
| 22 | SEQ ID NO: 1 | SEQ ID NO: 2 | | | SEQ ID NO: 5 | |
| 23 | SEQ ID NO: 1 | SEQ ID NO: 2 | | | SEQ ID NO: 5 | SEQ ID NO: 6 |
| 24 | SEQ ID NO: 1 | SEQ ID NO: 2 | | | | SEQ ID NO: 6 |
| 25 | SEQ ID NO: 1 | SEQ ID NO: 2 | SEQ ID NO: 3 | SEQ ID NO: 4 | | |
| 26 | SEQ ID NO: 1 | SEQ ID NO: 2 | SEQ ID NO: 3 | SEQ ID NO: 4 | SEQ ID NO: 5 | |
| 27 | SEQ ID NO: 1 | SEQ ID NO: 2 | SEQ ID NO: 3 | SEQ ID NO: 4 | SEQ ID NO: 5 | SEQ ID NO: 6 |
| 28 | SEQ ID NO: 1 | SEQ ID NO: 2 | SEQ ID NO: 3 | | SEQ ID NO: 5 | |
| 29 | SEQ ID NO: 1 | SEQ ID NO: 2 | SEQ ID NO: 3 | | SEQ ID NO: 5 | SEQ ID NO: 6 |
| 30 | SEQ ID NO: 1 | SEQ ID NO: 2 | SEQ ID NO: 3 | | | SEQ ID NO: 6 |
| 31 | | SEQ ID NO: 2 | | SEQ ID NO: 4 | | |
| 32 | | SEQ ID NO: 2 | | SEQ ID NO: 4 | SEQ ID NO: 5 | |
| 33 | | SEQ ID NO: 2 | | SEQ ID NO: 4 | SEQ ID NO: 5 | SEQ ID NO: 6 |
| 34 | | SEQ ID NO: 2 | | | SEQ ID NO: 5 | |
| 35 | | SEQ ID NO: 2 | | | SEQ ID NO: 5 | SEQ ID NO: 6 |
| 36 | | SEQ ID NO: 2 | | | | SEQ ID NO: 6 |
| 37 | | SEQ ID NO: 2 | SEQ ID NO: 3 | SEQ ID NO: 4 | | |
| 38 | | SEQ ID NO: 2 | SEQ ID NO: 3 | SEQ ID NO: 4 | SEQ ID NO: 5 | |
| 39 | | SEQ ID NO: 2 | SEQ ID NO: 3 | SEQ ID NO: 4 | SEQ ID NO: 5 | SEQ ID NO: 6 |
| 40 | | SEQ ID NO: 2 | SEQ ID NO: 3 | | SEQ ID NO: 5 | |
| 41 | | SEQ ID NO: 2 | SEQ ID NO: 3 | | SEQ ID NO: 5 | SEQ ID NO: 6 |
| 42 | | SEQ ID NO: 2 | SEQ ID NO: 3 | | | SEQ ID NO: 6 |
| 43 | | | SEQ ID NO: 3 | SEQ ID NO: 4 | | |
| 44 | | | SEQ ID NO: 3 | SEQ ID NO: 4 | SEQ ID NO: 5 | |
| 45 | | | SEQ ID NO: 3 | SEQ ID NO: 4 | SEQ ID NO: 5 | SEQ ID NO: 6 |
| 46 | | | SEQ ID NO: 3 | | SEQ ID NO: 5 | |
| 47 | | | SEQ ID NO: 3 | | SEQ ID NO: 5 | SEQ ID NO: 6 |
| 48 | | | SEQ ID NO: 3 | | | SEQ ID NO: 6 |
| 49 | SEQ ID NO: 7 | | | | | |
| 50 | SEQ ID NO: 7 | SEQ ID NO: 8 | | | | |
| 51 | SEQ ID NO: 7 | SEQ ID NO: 8 | SEQ ID NO: 9 | | | |
| 52 | | SEQ ID NO: 8 | | | | |
| 53 | | SEQ ID NO: 8 | SEQ ID NO: 9 | | | |
| 54 | | | SEQ ID NO: 9 | | | |
| 55 | | | | SEQ ID NO: 10 | | |
| 56 | | | | SEQ ID NO: 10 | SEQ ID NO: 11 | |
| 57 | | | | SEQ ID NO: 10 | SEQ ID NO: 11 | SEQ ID NO: 12 |
| 58 | | | | | SEQ ID NO: 11 | |
| 59 | | | | | SEQ ID NO: 11 | SEQ ID NO: 12 |

TABLE B-continued

|  | Light Chain | | | Heavy Chain | | |
|---|---|---|---|---|---|---|
| Antibody | CDR1 | CDR2 | CDR3 | CDR1 | CDR2 | CDR3 |
| 60 |  |  |  |  |  | SEQ ID NO: 12 |
| 61 | SEQ ID NO: 7 |  |  | SEQ ID NO: 10 |  |  |
| 62 | SEQ ID NO: 7 |  |  | SEQ ID NO: 10 | SEQ ID NO: 11 |  |
| 63 | SEQ ID NO: 7 |  |  | SEQ ID NO: 10 | SEQ ID NO: 11 | SEQ ID NO: 12 |
| 64 | SEQ ID NO: 7 |  |  |  | SEQ ID NO: 11 |  |
| 65 | SEQ ID NO: 7 |  |  |  | SEQ ID NO: 11 | SEQ ID NO: 12 |
| 66 | SEQ ID NO: 7 |  |  |  |  | SEQ ID NO: 12 |
| 67 | SEQ ID NO: 7 | SEQ ID NO: 8 |  | SEQ ID NO: 10 |  |  |
| 68 | SEQ ID NO: 7 | SEQ ID NO: 8 |  | SEQ ID NO: 10 | SEQ ID NO: 11 |  |
| 69 | SEQ ID NO: 7 | SEQ ID NO: 8 |  | SEQ ID NO: 10 | SEQ ID NO: 11 | SEQ ID NO: 12 |
| 70 | SEQ ID NO: 7 | SEQ ID NO: 8 |  |  | SEQ ID NO: 11 |  |
| 71 | SEQ ID NO: 7 | SEQ ID NO: 8 |  |  | SEQ ID NO: 11 | SEQ ID NO: 12 |
| 72 | SEQ ID NO: 7 | SEQ ID NO: 8 |  |  |  | SEQ ID NO: 12 |
| 73 | SEQ ID NO: 7 | SEQ ID NO: 8 | SEQ ID NO: 9 | SEQ ID NO: 10 |  |  |
| 74 | SEQ ID NO: 7 | SEQ ID NO: 8 | SEQ ID NO: 9 | SEQ ID NO: 10 | SEQ ID NO: 11 |  |
| 75 | SEQ ID NO: 7 | SEQ ID NO: 8 | SEQ ID NO: 9 | SEQ ID NO: 10 | SEQ ID NO: 11 | SEQ ID NO: 12 |
| 76 | SEQ ID NO: 7 | SEQ ID NO: 8 | SEQ ID NO: 9 |  | SEQ ID NO: 11 |  |
| 77 | SEQ ID NO: 7 | SEQ ID NO: 8 | SEQ ID NO: 9 |  | SEQ ID NO: 11 | SEQ ID NO: 12 |
| 78 | SEQ ID NO: 7 | SEQ ID NO: 8 | SEQ ID NO: 9 |  |  | SEQ ID NO: 12 |
| 79 |  | SEQ ID NO: 8 |  | SEQ ID NO: 10 |  |  |
| 80 |  | SEQ ID NO: 8 |  | SEQ ID NO: 10 | SEQ ID NO: 11 |  |
| 81 |  | SEQ ID NO: 8 |  | SEQ ID NO: 10 | SEQ ID NO: 11 | SEQ ID NO: 12 |
| 82 |  | SEQ ID NO: 8 |  |  | SEQ ID NO: 11 |  |
| 83 |  | SEQ ID NO: 8 |  |  | SEQ ID NO: 11 | SEQ ID NO: 12 |
| 84 |  | SEQ ID NO: 8 |  |  |  | SEQ ID NO: 12 |
| 85 |  | SEQ ID NO: 8 | SEQ ID NO: 9 | SEQ ID NO: 10 |  |  |
| 86 |  | SEQ ID NO: 8 | SEQ ID NO: 9 | SEQ ID NO: 10 | SEQ ID NO: 11 |  |
| 87 |  | SEQ ID NO: 8 | SEQ ID NO: 9 | SEQ ID NO: 10 | SEQ ID NO: 11 | SEQ ID NO: 12 |
| 88 |  | SEQ ID NO: 8 | SEQ ID NO: 9 |  | SEQ ID NO: 11 |  |
| 89 |  | SEQ ID NO: 8 | SEQ ID NO: 9 |  | SEQ ID NO: 11 | SEQ ID NO: 12 |
| 90 |  | SEQ ID NO: 8 | SEQ ID NO: 9 |  |  | SEQ ID NO: 12 |
| 91 |  |  | SEQ ID NO: 9 | SEQ ID NO: 10 |  |  |
| 92 |  |  | SEQ ID NO: 9 | SEQ ID NO: 10 | SEQ ID NO: 11 |  |
| 93 |  |  | SEQ ID NO: 9 | SEQ ID NO: 10 | SEQ ID NO: 11 | SEQ ID NO: 12 |
| 94 |  |  | SEQ ID NO: 9 |  | SEQ ID NO: 11 |  |
| 95 |  |  | SEQ ID NO: 9 |  | SEQ ID NO: 11 | SEQ ID NO: 12 |
| 96 |  |  | SEQ ID NO: 9 |  |  | SEQ ID NO: 12 |

In one embodiment, an antibody of the invention may comprise a light chain variable region comprising a CDR1 of amino acid sequence SEQ ID NO: 1 with zero to two amino acid substitutions, a CDR2 of amino acid sequence SEQ ID NO: 2 with zero to two amino acid substitutions, and a CDR3 of amino acid sequence SEQ ID NO:3 with zero to two amino acid substitutions, or may comprise a heavy chain variable region comprising a CDR1 of amino acid sequence SEQ ID NO: 4 with zero to two amino acid substitutions, a CDR2 of amino acid sequence SEQ ID NO: 5 with zero to two amino acid substitutions, and a CDR3 of amino acid sequence SEQ ID NO: 6 with zero to two amino acid substitutions. In a preferred embodiment, an antibody of the invention may comprise a light chain variable region comprising a CDR1 of amino acid sequence SEQ ID NO: 1 with zero to two amino acid substitutions, a CDR2 of amino acid sequence SEQ ID NO: 2 with zero to two amino acid substitutions, a CDR3 of amino acid sequence SEQ ID NO:3, a heavy chain variable region comprising a CDR1 of amino acid sequence SEQ ID NO: 4 with zero to two amino acid substitutions, a CDR2 of amino acid sequence SEQ ID NO: 5 with zero to two amino acid substitutions, and a CDR3 of amino acid sequence SEQ ID NO: 6 with zero to two amino acid substitutions. In an exemplary embodiment, an antibody of the invention may comprise a light chain variable region comprising a CDR1 of amino acid sequence SEQ ID NO: 1, a CDR2 of amino acid sequence SEQ ID NO: 2, a CDR3 of amino acid sequence SEQ ID NO:3, a heavy chain variable region comprising a CDR1 of amino acid sequence SEQ ID NO: 4, a CDR2 of amino acid sequence SEQ ID NO: 5, and a CDR3 of amino acid sequence SEQ ID NO: 6. The invention also encompasses the corresponding nucleic acid sequences of SEQ ID NO:1, 2, 3, 4, 5, and 6, which can readily be determined by one of skill in the art, and may be incorporated into a vector or other large DNA molecule, such as a chromosome, in order to express an antibody of the invention. In each of the above embodiments, the antibody may be humanized.

In another embodiment, an antibody of the invention may comprise a light chain variable region comprising a CDR1 of amino acid sequence SEQ ID NO: 7 with zero to two amino acid substitutions, a CDR2 of amino acid sequence SEQ ID NO: 8 with zero to two amino acid substitutions, and a CDR3 of amino acid sequence SEQ ID NO: 9 with zero to two amino acid substitutions, or may comprise a heavy chain variable region comprising a CDR1 of amino acid sequence SEQ ID NO: 10 with zero to two amino acid substitutions, a CDR2 of amino acid sequence SEQ ID NO: 11 with zero to two amino acid substitutions, and a CDR3 of amino acid sequence SEQ ID NO: 12 with zero to two amino acid substitutions. In a preferred embodiment, an antibody of the invention may comprise a light chain variable region comprising a CDR1 of amino acid sequence SEQ ID NO: 7 with zero to two amino acid substitutions, a CDR2 of amino acid sequence SEQ ID NO: 8 with zero to two amino acid substitutions, a CDR3 of amino acid sequence SEQ ID NO: 9 with zero to two amino acid substitutions, and a heavy chain variable region comprising a CDR1 of amino acid sequence SEQ ID NO: 10 with zero to two amino acid substitutions, a CDR2 of amino acid sequence SEQ ID NO:

11 with zero to two amino acid substitutions, and a CDR3 of amino acid sequence SEQ ID NO: 12 with zero to two amino acid substitutions. In an exemplary embodiment, an antibody of the invention may comprise a light chain variable region comprising a CDR1 of amino acid sequence SEQ ID NO: 7, a CDR2 of amino acid sequence SEQ ID NO: 8, a CDR3 of amino acid sequence SEQ ID NO: 9, a heavy chain variable region comprising a CDR1 of amino acid sequence SEQ ID NO: 10, a CDR2 of amino acid sequence SEQ ID NO: 11, and a CDR3 of amino acid sequence SEQ ID NO: 12. The invention also encompasses the corresponding nucleic acid sequences of SEQ ID NO: 7, 8, 9, 10, 11, and 12, which can readily be determined by one of skill in the art, and may be incorporated into a vector or other large DNA molecule, such as a chromosome, in order to express an antibody of the invention. In each of the above embodiments, the antibody may be humanized.

II. Methods of Using Anti-MIOX Antibodies

In an aspect, the present invention provides antibodies to detect MIOX in a biological sample obtained from a subject. In another aspect, the present invention provides antibodies to measure the amount of MIOX in a biological sample obtained from a subject. The amount of MIOX in a biological sample obtained from a subject can be used to classify a subject as having high or low amounts of MIOX, and may be further used to identify in the subject renal injury associated with proximal tubule injury.

(a) Methods to Detect and Measure the Amount of MIOX in a Biological Sample

In an aspect, the invention provides means to detect MIOX in a biological sample obtained from a subject. In another aspect, the invention provides means to measure the amount of MIOX in a biological sample obtained from a subject. The method generally comprises (i) obtaining a biological sample from a subject, and (ii) detecting and/or measuring the amount of MIOX in the sample using an antibody that specifically binds MIOX. Suitable antibodies are described above in Section I.

As used herein, the term "biological sample" refers to a sample obtained from a subject. Any biological sample containing MIOX is suitable. Numerous types of biological samples are known in the art. Suitable biological sample may include, but are not limited to, tissue samples or bodily fluids. In some embodiments, the biological sample is a tissue sample such as a tissue biopsy. The tissue biopsy may be a biopsy of kidney tissue. The biopsied tissue may be fixed, embedded in paraffin or plastic, and sectioned, or the biopsied tissue may be frozen and cryosectioned. Alternatively, the biopsied tissue may be processed into individual cells or an explant, or processed into a homogenate, a cell extract, a membranous fraction, or a protein extract. The sample may also be primary and/or transformed cell cultures derived from tissue from the subject. In other embodiments, the sample may be a bodily fluid. Non-limiting examples of suitable bodily fluids include blood, plasma, serum, and urine. The fluid may be used "as is", the cellular components may be isolated from the fluid, or a protein fraction may be isolated from the fluid using standard techniques.

Suitable subjects include, but are not limited to, a human, a livestock animal, a companion animal, a lab animal, and a zoological animal. A subject may or may not be known to have renal injury. In one embodiment, the subject may be a rodent, e.g. a mouse, a rat, a guinea pig, etc. In another embodiment, the subject may be a livestock animal. Non-limiting examples of suitable livestock animals may include pigs, cows, horses, goats, sheep, llamas and alpacas. In yet another embodiment, the subject may be a companion animal. Non-limiting examples of companion animals may include pets such as dogs, cats, rabbits, and birds. In yet another embodiment, the subject may be a zoological animal. As used herein, a "zoological animal" refers to an animal that may be found in a zoo. Such animals may include non-human primates, large cats, wolves, and bears. In preferred embodiments, the animal is a laboratory animal. Non-limiting examples of a laboratory animal may include rodents, canines, felines, and non-human primates. In certain embodiments, the animal is a rodent. In a preferred embodiment, the subject is human.

As will be appreciated by a skilled artisan, the method of collecting a biological sample can and will vary depending upon the nature of the biological sample and the type of analysis to be performed. Any of a variety of methods generally known in the art may be utilized to collect a biological sample. Generally speaking, the method preferably maintains the integrity of the sample such that MIOX can be accurately detected and the amount measured according to the invention.

Once a sample is obtained, it is processed in vitro to detect and measure the amount of MIOX using an anti-MIOX antibody. All suitable methods for detecting and measuring an amount of protein using an antibody known to one of skill in the art are contemplated within the scope of the invention. Methods for detecting and measuring an amount of protein using an antibody (i.e. "antibody-based methods") are well known in the art. Non-limiting examples include an ELISA, a sandwich immunoassay, a radioimmunoassay, an immunoblot or Western blot, flow cytometry, immunohistochemistry, and an array.

In general, an antibody-based method of detecting and measuring an amount of MIOX comprises contacting some of the sample, or all of the sample, comprising MIOX with an anti-MIOX antibody under conditions effective to allow for formation of a complex between the antibody and the MIOX protein. Typically, the entire sample is not needed, allowing one skilled in the art to repeatedly detect and measure the amount of MIOX in the sample. The method may occur in solution, or the antibody or MIOX protein comprising the sample may be immobilized on a solid surface. Non-limiting examples of suitable surfaces may include microtitre plates, test tubes, slides, beads, resins, and other polymers. Attachment to the substrate may occur in a wide variety of ways, as will be appreciated by those in the art. For example, the substrate and the antibody may be derivatized with chemical functional groups for subsequent attachment of the two. For example, the substrate may be derivatized with a chemical functional group including, but not limited to, amino groups, carboxyl groups, oxo groups or thiol groups. Using these functional groups, the antibody may be attached directly using the functional groups or indirectly using linkers. An anti-MIOX antibody may also be attached to the substrate non-covalently. For example, a biotinylated anti-MIOX antibody may be prepared, which may bind to surfaces covalently coated with streptavidin, resulting in attachment. Alternatively, an antibody may be synthesized on the surface using techniques such as photopolymerization and photolithography.

Contacting the sample with an antibody under effective conditions for a period of time sufficient to allow formation of a complex generally involves adding the anti-MIOX antibody composition to the sample and incubating the mixture for a period of time long enough for the anti-MIOX antibody to bind to any antigen present. After this time, the complex will be washed and the complex may be detected and the amount measured by any method well known in the art. Methods of detecting and measuring an amount of an antibody-polypeptide complex are generally based on the detection of a label or marker. The term "label", as used herein, refers to any substance attached to an antibody, or other substrate material, in which the substance is detectable by a detection method. Non-limiting examples of suitable labels include luminescent molecules, chemiluminescent molecules, fluorochromes, fluorescent quenching agents, colored molecules, radioisotopes, scintillants, biotin, avidin, stretpavidin, protein A, protein G, antibodies or fragments thereof, polyhistidine, $Ni^{2+}$, Flag tags, myc tags, heavy metals, and enzymes (including alkaline phosphatase, peroxidase, glucose oxidase, and luciferase). Methods of detecting and measuring an amount of an antibody-polypeptide complex based on the detection of a label or marker are well known in the art.

In some embodiments, an antibody-based method is an immunoassay. Immunoassays can be run in a number of different formats. Generally speaking, immunoassays can be divided into two categories: competitive immmunoassays and non-competitive immunoassays. In a competitive immunoassay, an unlabeled analyte in a sample competes with labeled analyte to bind an antibody. Unbound analyte is washed away and the bound analyte is measured. In a non-competitive immunoassay, the antibody is labeled, not the analyte. Non-competitive immunoassays may use one antibody (e.g. the capture antibody is labeled) or more than one antibody (e.g. at least one capture antibody which is unlabeled and at least one "capping" or detection antibody which is labeled.) Suitable labels are described above.

In other embodiments, an antibody-based method is an immunoblot or Western blot. In yet other embodiments, an antibody-based method is flow cytometry.

In different embodiments, an antibody-based method is immunohistochemistry (IHC). IHC uses an antibody to detect and quantify antigens in intact tissue samples. The tissue samples may be fresh-frozen and/or formalin-fixed, paraffin-embedded (or plastic-embedded) tissue blocks prepared for study by IHC. Methods of preparing tissue block for study by IHC, as well as methods of performing IHC are well known in the art.

In alternative embodiments, an antibody-based method is an array. An array comprises at least one address, wherein at least one address of the array has disposed thereon an anti-MIOX antibody. Arrays may comprise from about 1 to about several hundred thousand addresses. Several substrates suitable for the construction of arrays are known in the art, and one skilled in the art will appreciate that other substrates may become available as the art progresses. Suitable substrates are also described above. In some embodiments, the array comprises at least one anti-MIOX antibody attached to the substrate is located at one or more spatially defined addresses of the array. For example, an array may comprise at least one, at least two, at least three, at least four, or at least five anti-MIOX antibodies, each antibody recognizing the same or different epitope MIOX epitope, and each antibody may be may be at one, two, three, four, five, six, seven, eight, nine, ten or more spatially defined addresses.

In a preferred embodiment, a method for detecting MIOX and/or measuring the amount of MIOX in a biological sample is an immunoassay comprising at least one capture antibody and at least on capping antibody, wherein each antibody is an isolated anti-MIOX antibody and the capping antibody is attached to label. For example, an immunoassay may comprise at least one, at least two, at least three, at least four, or at least five capture antibodies, and at least one, at least two, at least three, at least four, or at least five capping antibodies. The capture antibody and the capping antibody may recognize the same MIOX epitope or, alternatively, the capture antibody and the capping antibody may each recognize a different MIOX epitope. When more than one capture antibody is used, the use of at least two antibodies that recognize distinct MIOX epitopes may increase the sensitivity of the assay. Non-limiting examples of suitable capture antibodies and suitable capping antibodies include the antibodies disclosed in Table B, as well as antibodies that specifically bind MIOX and recognize an epitope within an amino acid sequence selected from the group consisting of SEQ ID NO: 21 and SEQ ID NO:22. In some embodiments, a capture antibody is an isolated antibody that specifically binds MIOX and is listed in Table B. In other embodiments, a capping antibody is an isolated antibody that specifically binds MIOX and is listed in Table B. In still other embodiments, a capture antibody and a capping antibody are each an isolated antibody that specifically binds MIOX and are independently selected from the group consisting of the antibodies listed in Table B. In different embodiments, a capture antibody is an isolated antibody that specifically binds MIOX and recognizes an epitope within a sequence selected from the group consisting of SEQ ID NO: 21 and SEQ ID NO:22. In still different embodiments, a capping antibody is an isolated antibody that specifically binds MIOX and recognizes an epitope within a sequence selected from the group consisting of SEQ ID NO: 21 and SEQ ID NO:22.

In an exemplary embodiment, a capture antibody is an isolated antibody that specifically binds MIOX and recognizes an epitope within SEQ ID NO: 21 and a capping antibody is an isolated antibody that specifically binds MIOX and recognizes an epitope within SEQ ID NO: 22. In another exemplary embodiment, a capture antibody is an isolated antibody that specifically binds MIOX and recognizes an epitope within SEQ ID NO: 22 and a capping antibody is an isolated antibody that specifically binds MIOX and recognizes an epitope within SEQ ID NO: 21.

(b) Methods to Detect Renal Injury in a Subject

In aspect, the invention provides means to classify a subject based on the amount of MIOX measured in a biological sample obtained from the subject. The method generally comprises (i) obtaining a biological sample from a subject and measuring the amount of MIOX in the sample using an antibody that specifically binds MIOX, (ii) comparing the amount of MIOX in the sample to a reference value, and (iii) classifying the subject as having a high or low amount of MIOX based on the amount of MIOX measured in the sample. Methods for obtaining a biological sample from a subject and measuring the amount of MIOX in the sample using an antibody that specifically binds MIOX are detailed above and further described in the Examples. In a preferred embodiment, the biological sample is biological fluid selected from the group consisting of blood, plasma, serum, and urine.

Any suitable reference value known in the art may be used. For example, a suitable reference value may be the amount of MIOX in a biological fluid sample obtained from a subject or group of subjects of the same species that has normal renal function. In another example, a suitable reference value may be the amount of MIOX in biological fluid sample obtained from a subject or group of subjects of the same species that has renal injury as measured by creatinine or other non-specific biomarker of renal function but that has proximal tubule injury. In another example, a suitable reference value may be a measurement of the amount of MIOX in a reference sample obtained from the same subject. The reference sample comprises the same type of biological fluid as the test sample, and may or may not be obtained from the subject when renal function was normal. A skilled artisan will appreciate that it is not always possible or desirable to obtain a reference sample from a subject when the subject is otherwise healthy. For example, in an acute setting, a reference sample may be the first sample obtained from the subject at presentation. In another example, when monitoring the effectiveness of a therapy, a reference sample may be a sample obtained from a subject before therapy began.

According to the invention, a subject may be classified based on the amount of MIOX measured in the sample. Classifying a subject based on the amount of MIOX measured in a sample of biological fluid obtained from the subject may be used to identify subjects with renal injury. The term "renal injury" is described in detail below. Generally speaking, a subject may be classified as having a high or low amount of MIOX compared to a reference value, wherein a high amount of MIOX is an amount above the reference value and a low amount is an amount equal to or below the reference value. In preferred embodiments, to classify a subject as having a high amount of MIOX, the amount of MIOX in the sample compared to the reference value may be at least 5% greater. For example, the amount of MIOX in the sample may be at least 5%, at least 10%, at least 20%, at least 30%, at least 40%, at least 50%, at least 60%, at least 70%, at least 80%, at least 90%, or at least 100% greater than the reference value. In other embodiments, the amount of MIOX in the sample of biological fluid obtained from the subject compared to the reference value may be increased at least 2-fold. For example, the amount of MIOX in the sample compared to the reference value may be increased at least 2-fold, at least 5-fold, at least 10-fold, at least 15-fold, at least 20-fold, at least 25-fold, at least 30-fold, at least 35-fold, at least 40-fold, at least 45-fold, or at least 50-fold.

In another aspect, the invention provides means to detect renal injury in a subject. As used herein, the term "renal injury" refers to a loss of kidney function. The causes of renal injury known in the art are numerous, and may include, but are not limited to, necrosis, ischemia, vascular damage, exposure to substances that damage the kidney such as toxins, intravenous contrast, antibiotics, pigments, and LPS, obstruction of the urinary tract, and trauma or crush injury to the kidney. Further by "renal injury" is meant acute kidney injury, as defined according to the Acute Kidney Injury Network criteria (see Metha et al. Cri Care 2007). Biomarkers of kidney function are well known in the art. Non-limiting examples of biomarkers of renal injury include increased proteinuria, a rise in serum creatinine, a reduction in urine output, and an increase in blood urea nitrogen. Evidence of renal injury may also be obtained histologically. Applicants have also discovered that increased MIOX in a biological fluid is also a biomarker of renal injury. In a preferred embodiment, the invention provides means to detect renal injury directly or indirectly associated with proximal tubule injury.

In an aspect, the invention provides means to detect proximal tubule injury in a subject. The proximal tubule is the portion of the duct system of the nephron of the kidney which leads from Bowman's capsule to the loop of Henle. The causes of proximal tube injury are known in the art and may include, but are not limited to, necrosis, ischemia, vascular damage, exposure to substances that damage the kidney such as toxins, antibiotics, pigments, and LPS, obstruction of the urinary tract, and trauma or crush injury to the kidney. Applicants have discovered that increased MIOX in a biological fluid is also a biomarker of proximal tubule injury. Non-specific biomarkers of renal injury, such as serum creatinine or other non-specific markers known in the art, may or may not indicate the presence of proximal tubule cell damage. In a preferred embodiment, the invention provides means to detect renal injury directly or indirectly associated with proximal tubule cell damage.

For each aspect, the method generally comprises (i) obtaining a biological sample from a subject, (ii) measuring the amount of MIOX in the sample using an antibody that specifically binds MIOX, and (iii) comparing the amount of MIOX in the sample to a reference value. A greater amount of MIOX in the sample compared to the reference value indicates renal injury, proximal tubular injury, proximal tubular cell death, protein loss from the proximal tubules, or a combination thereof. The amount of MIOX may be a qualitative, a semi-quantitative or quantitative measurement. Suitable anti-MIOX antibodies are described above, as are methods for measuring the amount of MIOX in a biological sample. In a preferred embodiment, the biological sample is biological fluid selected from the group consisting of blood, plasma, serum, and urine.

TABLE C

Sequence listings

| SEQ ID NO: | Description | SEQUENCE |
|---|---|---|
| 1 | mAb 01D10 LC CDR1 | SGNIHNYLA |
| 2 | mAb 01D10 LC CDR2 | NAKTLADGVPS |
| 3 | mAb 01D10 LC CDR3 | QHFWSIPFT |
| 4 | mAb 01D10 HC CDR1 | TSYYIH |
| 5 | mAb 01D10 HC CDR2 | WIYPGSGNSKYNE |
| 6 | mAb 01D10 HC CDR3 | YYCARDGST |

TABLE C-continued

Sequence listings

| SEQ ID NO: | Description | SEQUENCE |
|---|---|---|
| 7 | mAb 12H06 LC CDR1 | SKSVSTSGY |
| 8 | mAb 12H06 LC CDR2 | LLIYLASNLES |
| 9 | mAb 12H06 LC CDR3 | TYYCQHSRE |
| 10 | mAb 12H06 HC CDR1 | TSYWMH |
| 11 | mAb 12H06 HC CDR2 | LIDPSDSYTNYNQ |
| 12 | mAb 12H06 HC CDR3 | YYCVRTYYH |
| 13 | mAb 01D10 LC variable domain | DIQMTQSPASLSASVGETVTITCRTSGNIHNYLAWYQQKQGKSPQLLVYNAKTLADGVPSRFSGSG SGTQYSLKINSLQPEDFGSYYCQHFWSIPFTFGSGTKLEIKRAD |
| 14 | mAb 01D10 HC variable domain | QVQLQQSGPELVKPGASVKISCKASGYSFTSYYIHWVKQRPGQGLEWIGWIYPGSGNSKYNEKFKG KATLTADTSSSTAYMQLSSLTSEDSAVYYCARDGSTYNWNFDVWGTGTTVTVSSAKTTPPSVYP |
| 15 | mAb 12H06 LC variable domain | DIVVTQSPASFAVSLGQRATISCRASKSVSTSGYSYINWYQQKPGQPPKLLIYLASNLESGVPARFSG SGSGTDFTLNIHPVEEEDAATYYCQHSRELPLTFGAGTRLELK |
| 16 | mAb 12H06 HC variable domain | QVQLQQPGAELVRPGTSVKLSCKASGYTFTSYWMHWVKQRPGQGLEWIGLIDPSDSYTNYNQKFK GKATLTVDTSSSTASMQLSSLTSEDSAVYYCVRTYYHSSYFFAYWGQGTLVTVSSAKTTPPSVYP |
| 17 | mAb 01D10 LC variable domain | GACATCCAGATGACCCAGTCTCCAGCCTCCCTATCTGCATCTGTGGGAGAAACTGTCACCATCA CATGTCGAACAAGTGGGAATATTCACAATTATTTAGCATGGTATCAGCAGAAACAGGGAAAATCT CCTCAGCTCCTGGTCTATAATGCAAAAACCTTAGCAGATGGTGTGCCATCAAGGTTCAGTGGCA GTGGATCAGGAACACAATATTCTCTCAAGATCAACAGCCTGCAACCTGAAGATTTTGGGAGTTAT TACTGTCAACATTTTTGGAGTATTCCATTCACGTTCGGCTCGGGGACAAAGTTGGAAATAAAACG GCTGAT |
| 18 | mAb 01D10 HC variable domain | CAGGTCCAGCTGCAGCAGTCTGGACCTGAGCTGGTGAAGCCTGGGGCTTCAGTGAAGATATCC TGCAAGGCTTCTGGCTACAGCTTCACAAGCTACTATATACACTGGGTGAAGCAGAGGCCTGGAC AGGGACTTGAGTGGATTGGATGGATTTATCCTGGAAGTGGTAATTCTAAGTACAATGAGAAGTTC AAGGGCAAGGCCACACTGACGGCAGACACATCCTCCAGTACTGCCTACATGCAACTCAGCAGC CTAACATCTGAGGACTCTGCGGTCTATTACTGTGCAAGAGACGGTAGTACCTACAACTGGAACT TCGATGTCTGGGGCACAGGGACCACGGTCACCGTCTCCTCAGCCAAAACAACACCCCCATCAG TCTATCCA |
| 19 | mAb 12H06 LC variable domain | GACATTGTGGTGACACAGTCTCCTGCTTCCTTTGCTGTATCTCTGGGGCAGAGGGCCACCATCT CATGCAGGGCCAGCAAAAGTGTCAGTACATCTGGCTATAGTTATATAAACTGGTACCAACAGAA ACCAGGACAGCCACCCAAACTGCTCATCTATCTTGCATCCAACCTAGAATCTGGGGTCCCTGCC AGGTTCAGTGGCAGTGGGTCTGGGACAGACTTCACCCTCAACATCCATCCTGTGGAGGAGGAG GATGCTGCAACCTAtTACTGTCAGCACAGTAGGGAGCTTCCTCTCACGTTCGGTGCTGGGACCA GGCTGGAGCTGAAA |
| 20 | mAb 12H06 HC variable domain | CAGGTCCAACTGCAGCAGCCTGGGGCTGAACTGGTGAGGCCTGGGACTTCAGTGAAATTGTCC TGCAAGGCTTCTGGCTACACCTTCACCAGCTACTGGATGCACTGGGTTAAACAGAGGCCTGGAC AAGGCCTTGAGTGGATCGGTCTGATTGATCCTTCTGATAGTTATACTAACTACAATCAAAAGTTC AAGGGCAAGGCCACATTGACTGTAGACACATCCTCCAGCACAGCCTCCATGCAACTCAGCAGC CTGACATCTGAGGACTCTGCGGTCTATTACTGTGTAAGAACTTACTACCATAGTAGCTACTTCTT TGCTTACTGGGGCCAAGGGACTCTGGTCACTGTCTCTTCAGCCAAAACAACACCCCCATCAGTC TATCCA |
| 21 | 12H06 human MIOX epitope | RPYYQGLIDKYC |
| 22 | 01D10 human MIOX epitope | PSLVYRPDVDPEV |
| 23 | N-terminus of MIOX | GSPEFKVTVG |
| 24 | N-terminus of GST | MSPILGYWKI |

TABLE C-continued

Sequence listings

| SEQ ID NO: | Description | SEQUENCE |
|---|---|---|
| 25 | Epitope of rabbit polyclonal antibody R9544 | MKVTVGPDPSLVYRPDVDPEVAKDKASFR |
| 26 | Epitope of rabbit polyclonal antibody R9544 | GLVDESDPDVDFPNSF |
| 27 | Epitope of rabbit polyclonal antibody R9544 | DSTFQDNPDLQDPR |
| 28 | Epitope of rabbit polyclonal antibody R9544 | QGLIDKYCPG |
| 29 | Amino acid sequence of human MIOX | MKVTVGPDPS LVYRPDVDPE VAKDKASFRN YTSGPLLDRV FTTYKLMHTH QTVDFVRSKH AQFGGFSYKK MTVMEAVDLL DGLVDESDPD VDFPNSFHAF QTAEGIRKAH PDKDWFHLVG LLHDLGKVLALFGEPQWAWGDTFPVGCRPQASVVFCDSTFQDNPDLQDPRYSTELGMYQ PHCGLDRVLMSWGHDEYMYQVMKFNKFSLPPEAFYMIRFHSFYPWHTGRDYQQLCSQQDL AMLPWVREFNKFDLYTKCPDLPDVDKLRPYYQGLIDKYCPGILSW |
| 30 | Portion of MIOX sequence, Mouse or Rat | PSLVYRPDVDPEM |
| 31 | Portion of MIOX sequence, Pig or Cat | PSLVYRPDVDPEA |
| 32 | Portion of MIOX sequence, Guinea Pig | PSLIYRPDMDPEM |
| 33 | Portion of MIOX sequence, Ground Squirrel | PSLVYRPDVGTEA |
| 34 | Portion of MIOX sequence, Dog | PSLVYRPDMDPEK |

EXAMPLES

The following examples are included to demonstrate preferred embodiments of the invention. It should be appreciated by those of skill in the art that the techniques disclosed in the examples that follow represent techniques discovered by the inventors to function well in the practice of the invention. Those of skill in the art should, however, in light of the present disclosure, appreciate that many changes can be made in the specific embodiments that are disclosed and still obtain a like or similar result without departing from the spirit and scope of the invention, therefore all matter set forth or shown in the accompanying examples and drawings is to be interpreted as illustrative and not in a limiting sense Antibodies specific for the MIOX protein were generated as described below in Example 2 and in the Methods. Specifically, two hybridomas were generated and two antibodies were obtained from the hybridomas.

Figure 1B:
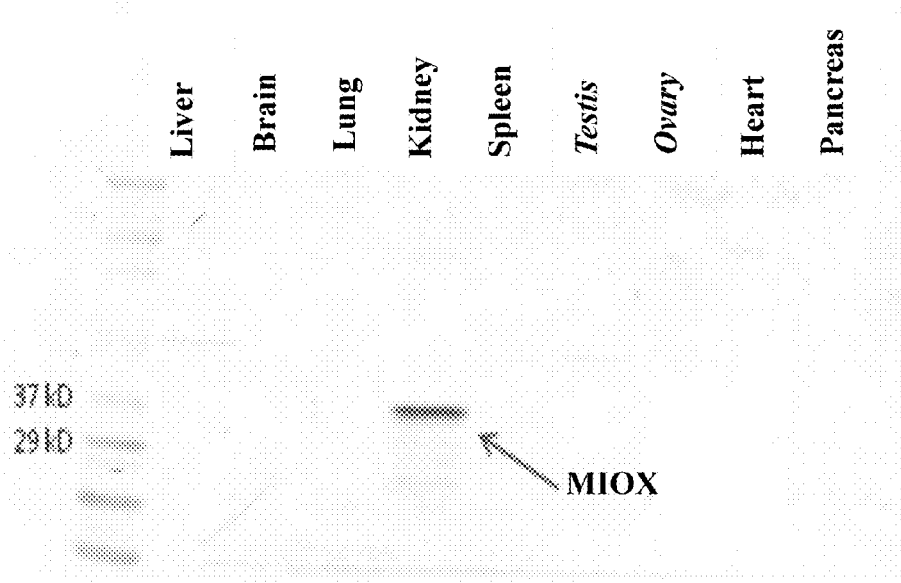

Example 1: Identification of Myo-Inositol Oxygenase as a Renal Specific Biomarker We sought to identify mouse genes that were expressed in the kidney by a factor of at least 10-fold compared with other tissues. Previous studies by Laterza, et al. dissected brain, liver, spleen, kidney, skeletal muscle, lung, pancreas, heart, and small intestine from 3 (2 male and 1 female) C57Bl/6 mice (Laterza et al. Clin Chem. 2006; 52:1713). This previously generated data was mined for genes that had mean signal intensity of >10,000, were expressed at >10-fold amounts in the kidney relative to the other tissues, and were expressed in the renal proximal tubule. Using this strategy, Miox was identified as a renal specific, abundant gene (FIG. 1A). The Miox gene encodes the protein myo-inositol oxygenase (Miox). In order to confirm the tissue specific nature of the human homolog of Miox, hereinafter abbreviated MIOX, human tissue homogenates from liver, brain, lung, kidney, spleen, testis, ovary, heart, and pancreas were probed using an anti-MIOX rabbit polyclonal antibody. Consistent with the mouse gene profiling data, MIOX protein was only detected in human kidney homogenate (FIG. 1B) (Gaut J P, et al. Clin Chem. 2014:60(5):747-57).

Example 2: Characterization of Anti-MIOX Antibodies

Figure 3A:
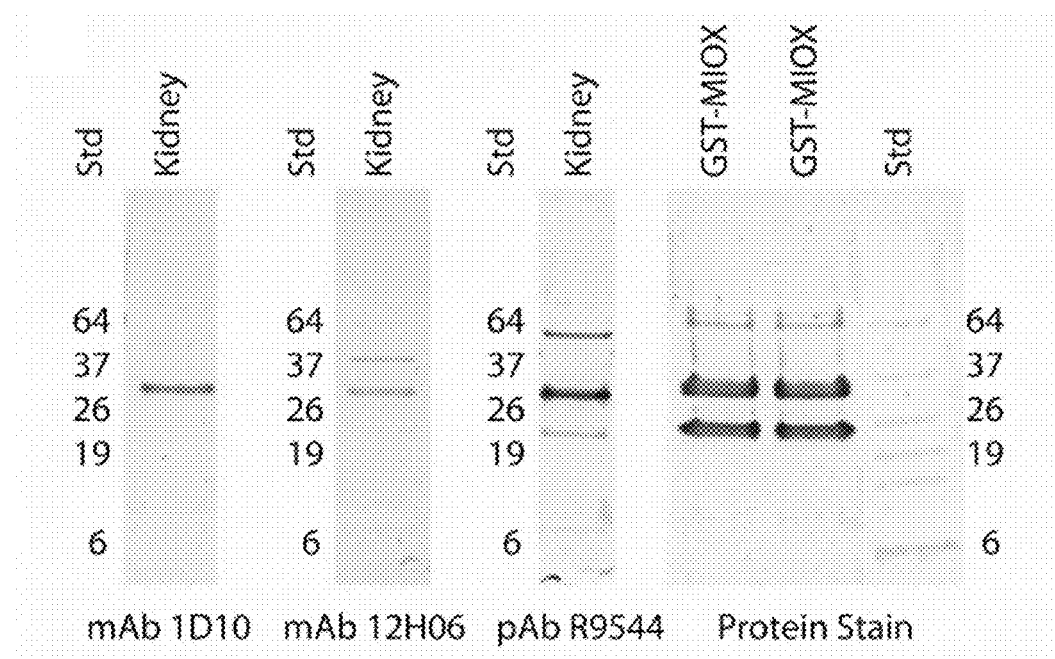

Rabbit polyclonal and mouse monoclonal anti-MIOX antibodies were generated using recombinant GST-tagged MIOX as antigen. To confirm the identity of recombinant GST-MIOX, the protein was first cleaved into GST and MIOX with thrombin. The cleaved proteins were separated by use of SDS-PAGE and subjected to Edman sequencing (FIG. 3A). The protein migrating between 26 and 37 kDa gave a sequence of GSPEFKVTVG (SEQ ID NO:23) corresponding to the N-terminus of MIOX. The protein near 26 kDa gave a sequence of MSPILGYWKI (SEQ ID NO:24) corresponding to the N-terminus of S. japonicum GST. Both monoclonal antibodies were isotyped and found to be $IgG_{2bK}$. Western blots were used to confirm the antibodies' ability to recognize recombinant MIOX and endogenous MIOX present in normal human kidney homogenate (FIG. 3A). The polyclonal and monoclonal antibodies recognized a protein with molecular mass between 26 and 37 kDa that comigrated with the recombinant MIOX protein (FIG. 3A). These results are consistent with the expected molecular weight of MIOX, 33 kDa.

Figure 3B:
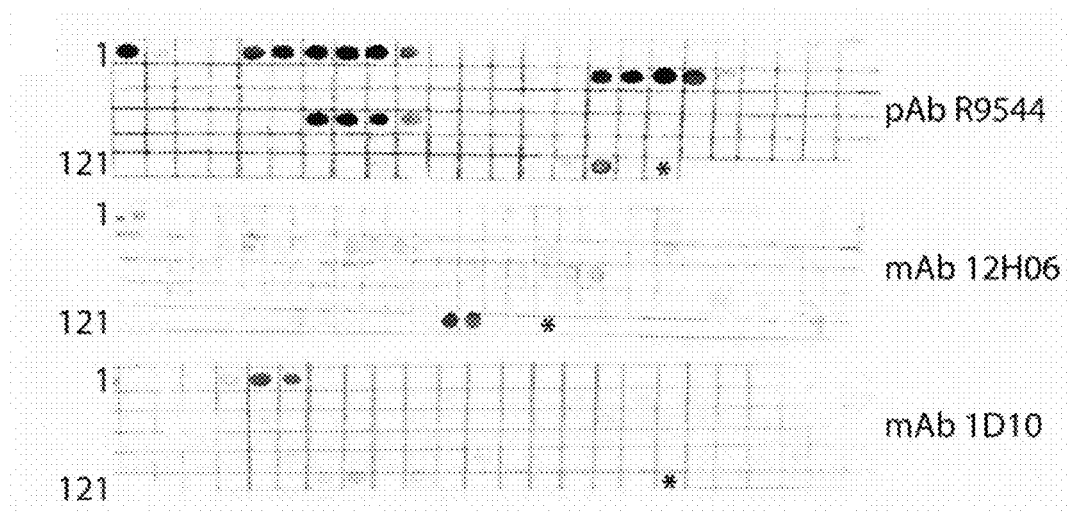
Figure 3D:
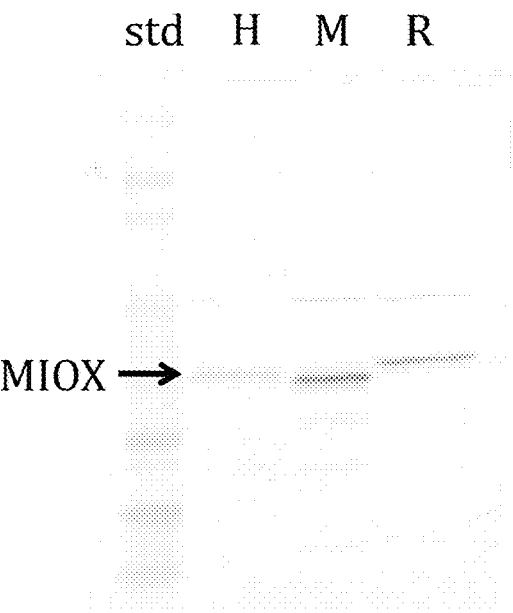
Figure 3E:
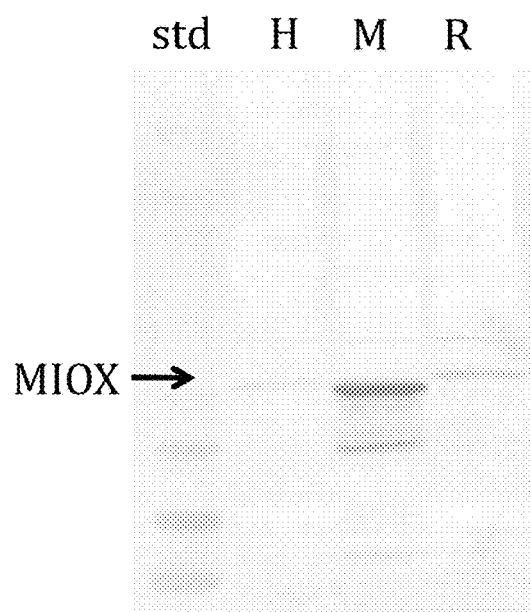

The cross-species immunoreactivity of the anti-MIOX monoclonal antibodies was investigated (FIG. 3D,E). Human, mouse, and rat kidney homogenates were separately probed with both monoclonal anti-MIOX antibodies. All three homogenates showed immunoreactivity at the expected molecular weight of endogenous MIOX.

Figure 4A:
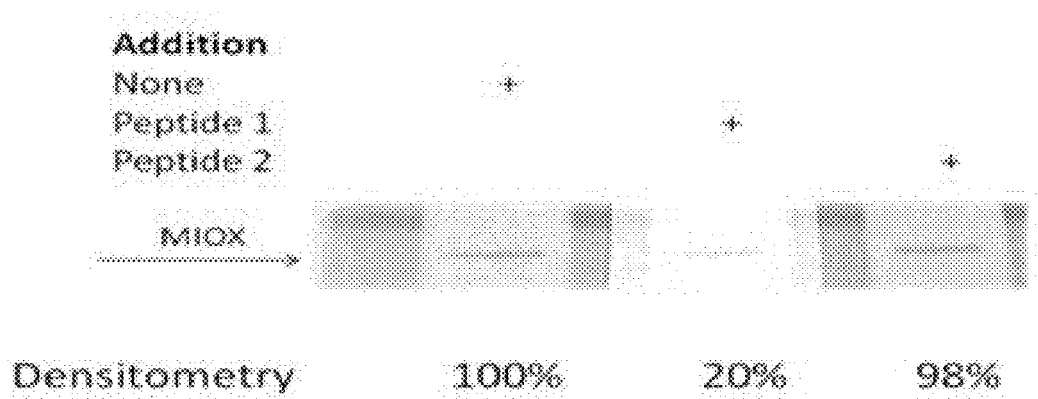
FIG. 4A and FIG. 4B depict images of immunoblots showing confirmation of specific antibody epitopes by blocking mAb binding to endogenous MIOX.
Figure 4B:
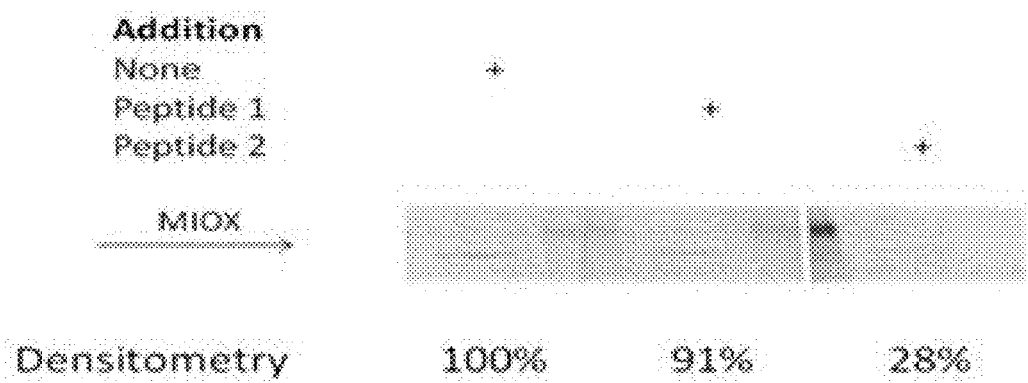

The linear epitopes of the anti-MIOX antibodies were determined by use of spot-peptide membrane arrays containing the full length amino acid sequence of MIOX. The two mouse monoclonal antibodies mapped to opposite ends of the MIOX sequence (FIG. 3B). The antibody designated 01D10 mapped to the N-terminal sequence of MIOX (FIG. 3C). The peptide spots were decoded to reveal the sequence P9-V21. The mouse monoclonal antibody designated 12H06 mapped to the C-terminal region of MIOX (FIG. 3C). The peptide spots were decoded to reveal the epitope sequence R268-C279. Human MIOX showed 89.8% homology to mouse Miox and 90.5% homology to rat Miox. The peptide epitope recognized by the 12H06 mouse monoclonal antibody was 100% identical to the corresponding mouse and rat Miox peptide sequence. The peptide epitope recognized by the 01D10 mouse monoclonal antibody was 92% identical to the corresponding mouse and rat Miox peptide sequence. The epitope recognized by the 01D10 mouse monoclonal antibody differed by 1 amino acid: the valine at amino acid position 21 is replaced by a methionine in mouse Miox. The rabbit anti-MIOX polyclonal antibody R9544 demonstrated 5 regions of intense staining, a finding consistent with the polyclonal nature of this antibody (FIG. 3C). Each monoclonal epitope sequence was validated for its uniqueness in a nonredundant Homo sapiens database by use of BLAST. A critical output parameter from BLAST is the expected value (E value). The E value is a measure of the chance that a random alignment from the probed database would produce the same normalized score. On the basis of the E value, there is a <1 in >1 000 000 chance that the epitope sequences could be randomly found in the database (data not shown). The lowest E value of a non-MIOX protein was 2.3, compared to a MIOX E value of $1\times10^{-6}$, indicating the highly specific nature of the antibody epitopes. Individual peptides corresponding to the mapped epitopes for both monoclonal antibodies were produced. Preincubation by use of the N-terminal peptide epitope, but not the C-terminal peptide epitope, inhibited binding of the 01D10 mouse monoclonal anti-MIOX antibody to a MIOX spot-peptide array (FIG. 4A). Similarly, preincubation by use of the C-terminal peptide epitope, but not the N-terminal peptide epitope, inhibited binding of the 12H06 mouse monoclonal anti-MIOX antibody to a MIOX spot-peptide array (FIG. 4B).

Example 3: Immunohistochemical Analysis of MIOX in Human Kidney

Figures 2A, 2B:
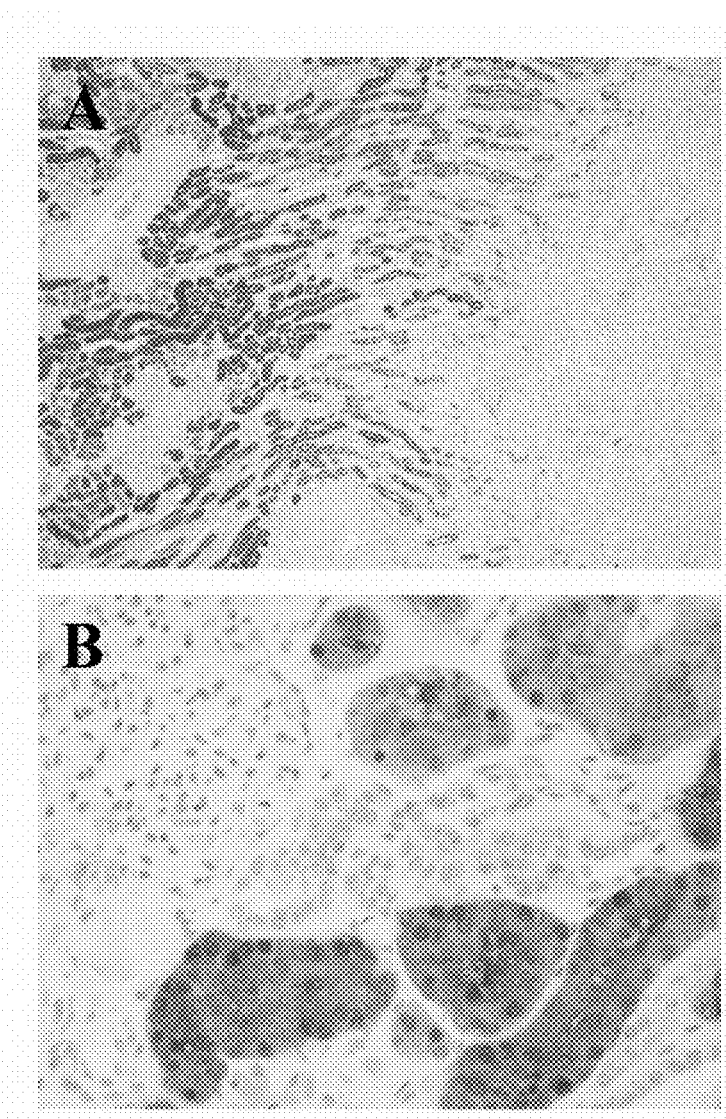
FIG. 2A and FIG. 2B depict micrographs showing MIOX expression in normal human kidney. Formalin-fixed paraffin embedded human kidney tissue was stained using the rabbit polyclonal anti-MIOX antibody R9544.

Human kidney tissues were obtained from the uninvolved portions of partial nephrectomy specimens from patients with renal cell carcinoma. Single formalin-fixed paraffin embedded sections were stained with rabbit polyclonal anti-MIOX antibody. Consistent with previous studies, the MIOX protein showed strong immunoreactivity in the proximal tubules (FIG. 2A,B) (Hu E, et al. Am J Physiol Renal Physiol. 2000; 279:F426; Arner R J et al. Biochem Biophys Res Commun 2006; 339:816).

Example 4: MIOX Immunoassay

The mouse monoclonal antibodies were optimized for use in a sandwich immunoassay. The monoclonal antibody designated 12H06 was used as a capture antibody and biotinylated monoclonal antibody 01D10 was used as a capping antibody. The limit of detection, defined as a signal-to-noise ratio of 2 relative to background, was 115 (55) pg/mL [n=13, mean (SD)] (Table 1). Human plasma samples stored at 4° C. or −80° C. for 10 days showed no significant difference in MIOX concentration [absolute mean % difference=7.4% (4.0%), mean % difference=− 0.4% (9.4%); n=4]. The interassay coefficient of variation (CV) was determined by calculating the median concentration of 3 samples on 3 separate days. The interassay CV was 15.2% (3.4%) [mean MIOX concentration 5.6 (0.7) ng/mL, n=9]. All samples underwent 2 freeze-thaw cycles. The intra-assay CV, determined by use of 19 plasma samples with a mean MIOX concentration of 21.2 ng/mL, range 1.7-48.2 ng/mL, was 7.9% (5.2%). GST-MIOX spiked into human heparinized plasma demonstrated 94% (19%) recovery of the expected signal (n=8). The MIOX immunoassay demonstrated dilutional linearity recovery of 109% (12%) (n=9).

TABLE 1

MIOX immunoassay performance characteristics.

| | |
|---|---|
| Interassay CV | 15.2 ± 3.4%, n = 9 |
| Intraassay CV | 7.2 ± 5.2%, n = 19 |
| LOD (pg/mL) | 115 ± 55, n = 13 |
| Spike/recovery | 94 ± 19%, n = 8 |
| Dilutional linearity recovery | 109 ± 12%, n = 9 |

Abbreviations:
CV—coefficient of variation;
LOD—limit of detection

Example 5: Mouse AKI Model

Figure 5A:
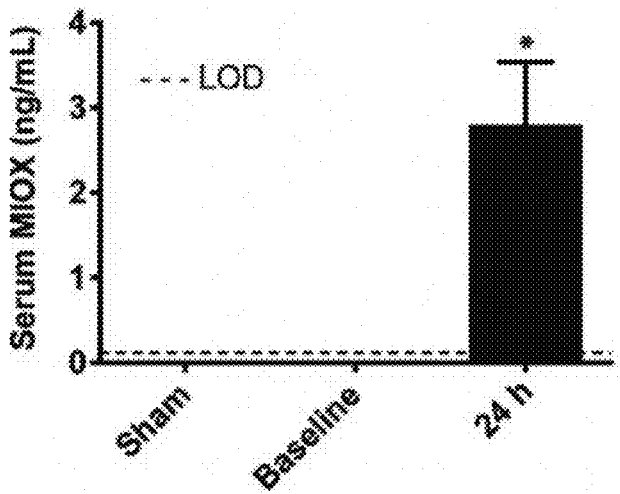
FIG. 5A, FIG. 5B, FIG. 5C and FIG. 5D depict results from the mouse AKI model.
Figure 5B:
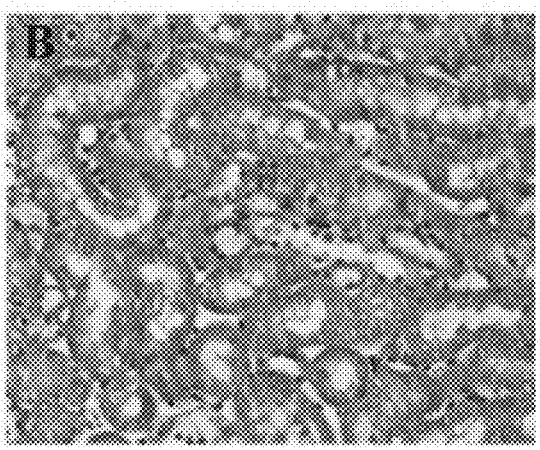
Figure 5C:
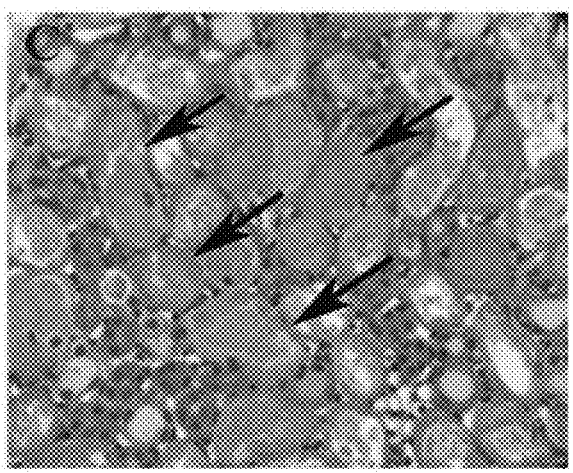
Figure 5D:
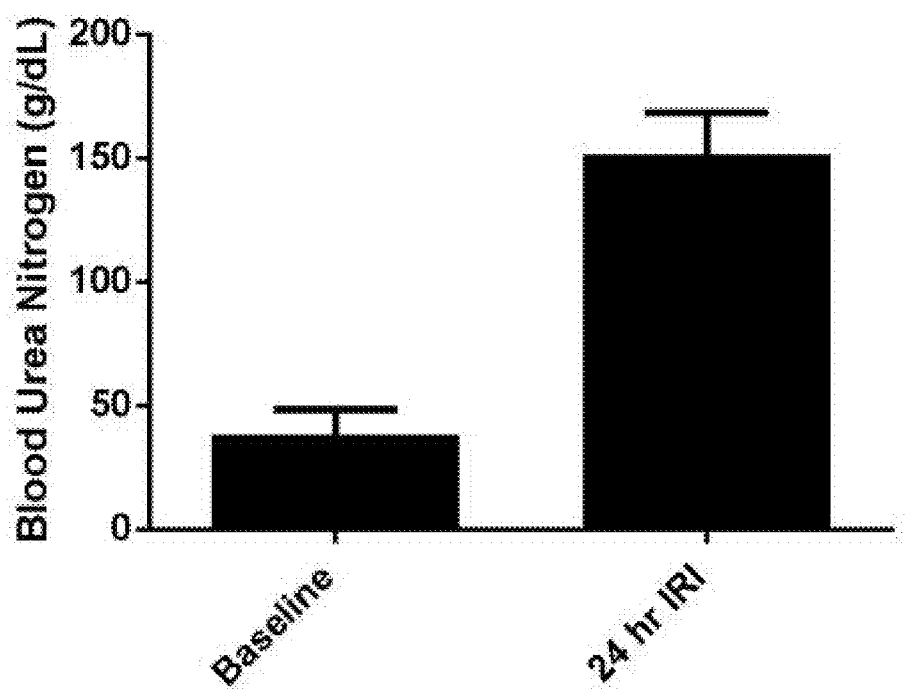

A mouse model of kidney ischemia-reperfusion injury, which mimics clinical AKI, was used as a proof of concept study to assess the specificity and sensitivity of MIOX for AKI. Animals were subjected to bilateral renal artery clamping for 30 minutes to induce AKI. Blood and urine MIOX levels are correlated with histologic evidence of kidney injury, serum creatinine, and blood urea nitrogen at multiple time points. Histologic staining was performed according to standard procedures, as was measurement of blood urea nitrogen. FIG. 5D depicts blood urea nitrogen levels at baseline and 24 h after injury. Miox was not detected in the serum of normal or sham-operated mice 24 h postoperatively (FIG. 5A). In contrast, Miox was markedly increased in the serum of mice 24 h after 30 min of bilateral ischemia reperfusion injury (FIG. 5A). Histologic examination of kidneys from sham-operated animals showed no evidence of tubular necrosis (FIG. 5B). In contrast, histologic examination revealed significant tubular necrosis in the kidneys of the experimental mice 24 h after injury (FIG. 5C).

Example 6: Analysis of Plasma from Acute Kidney Injury Patients

Figure 6A:
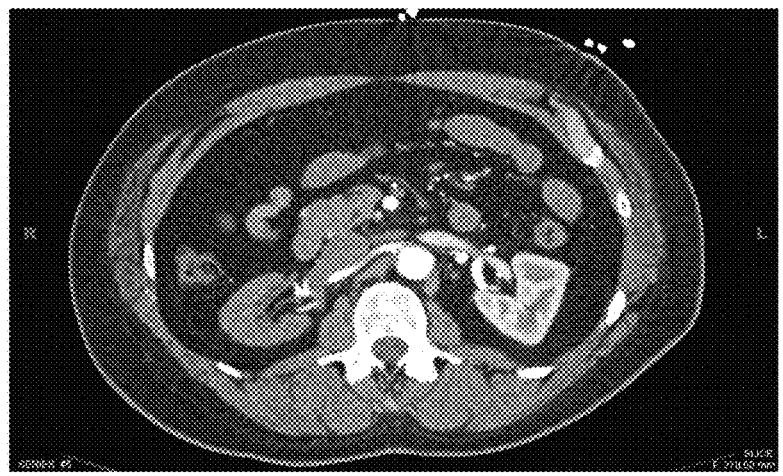
FIG. 6A, FIG. 6B and FIG. 6C show detailed information for a single patient with acute kidney injury.
Figure 6B:
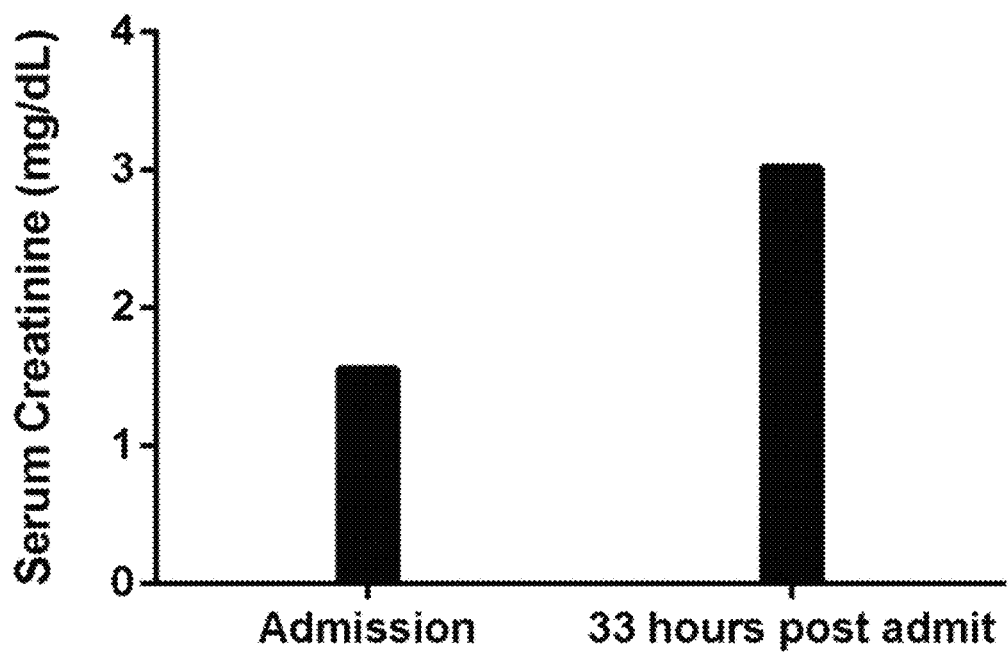
Figure 6C:
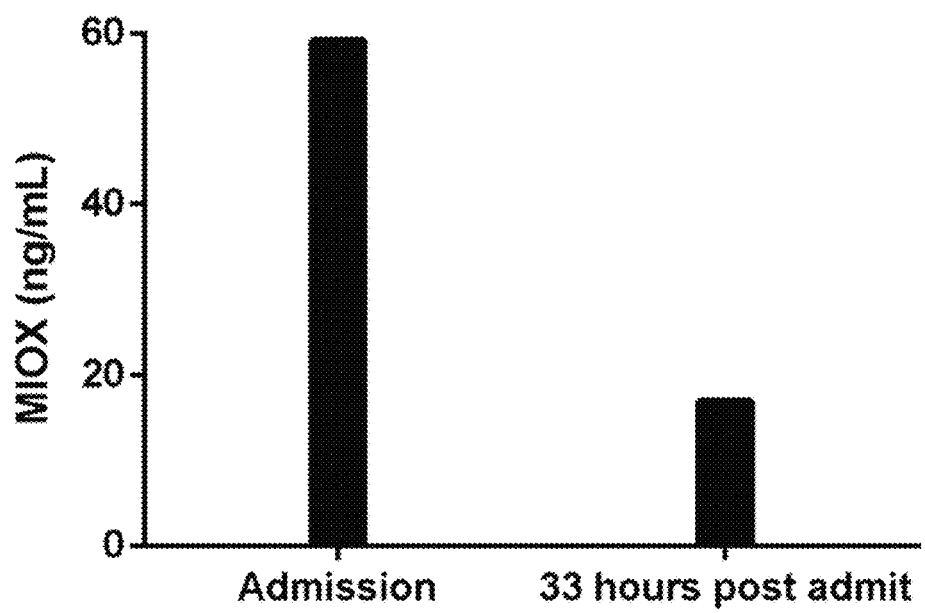
Figure 7A:
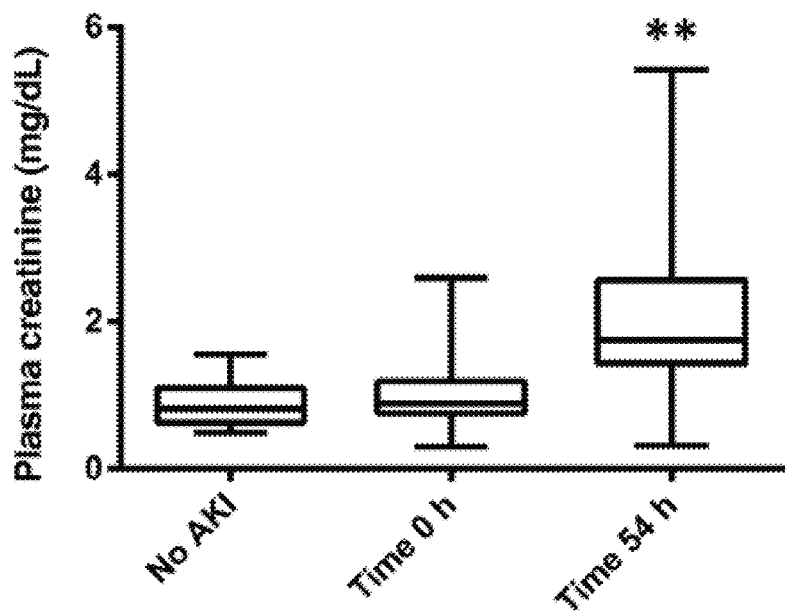
FIG. 7A and FIG. 7B show MIOX in critically ill and hospitalized patients.
Figure 7B:
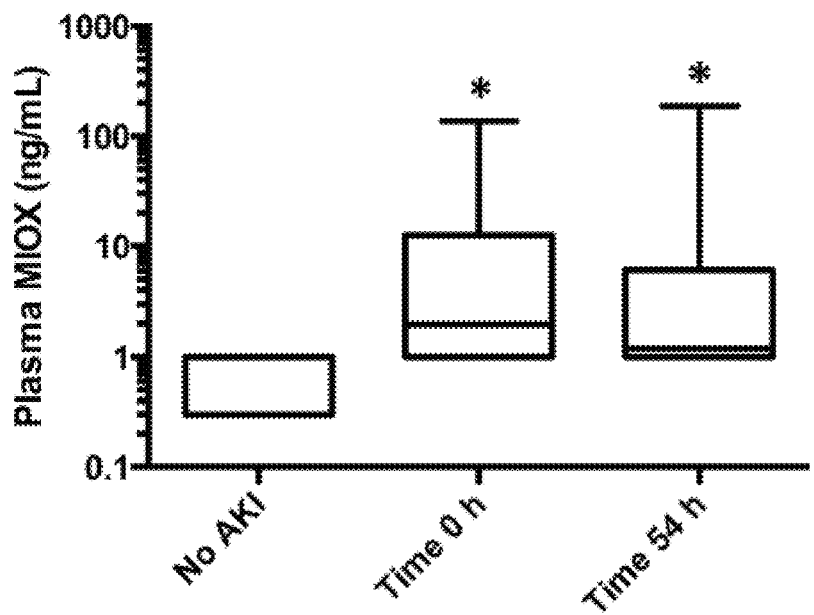
Figure 8A:
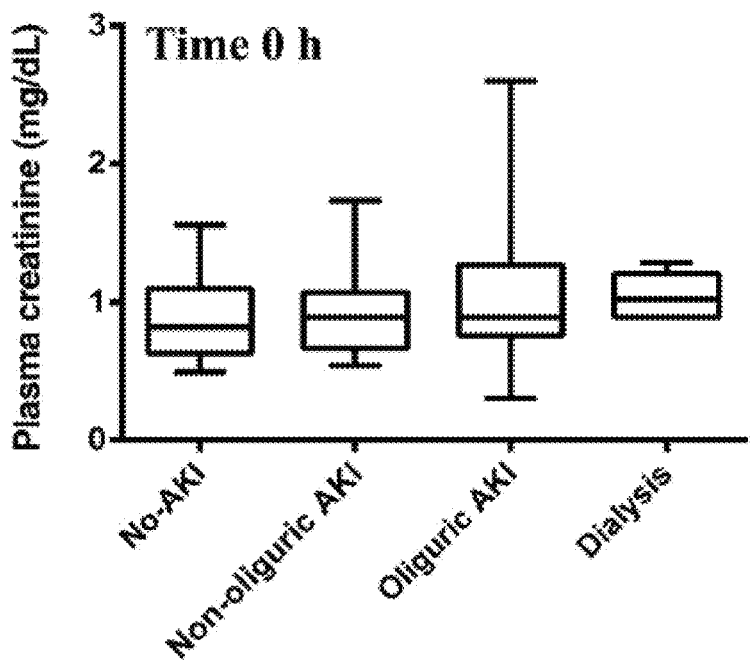
FIG. 8A, FIG. 8B, FIG. 8C and FIG. 8D depict MIOX and creatinine levels in AKI patients.
Figure 8B:
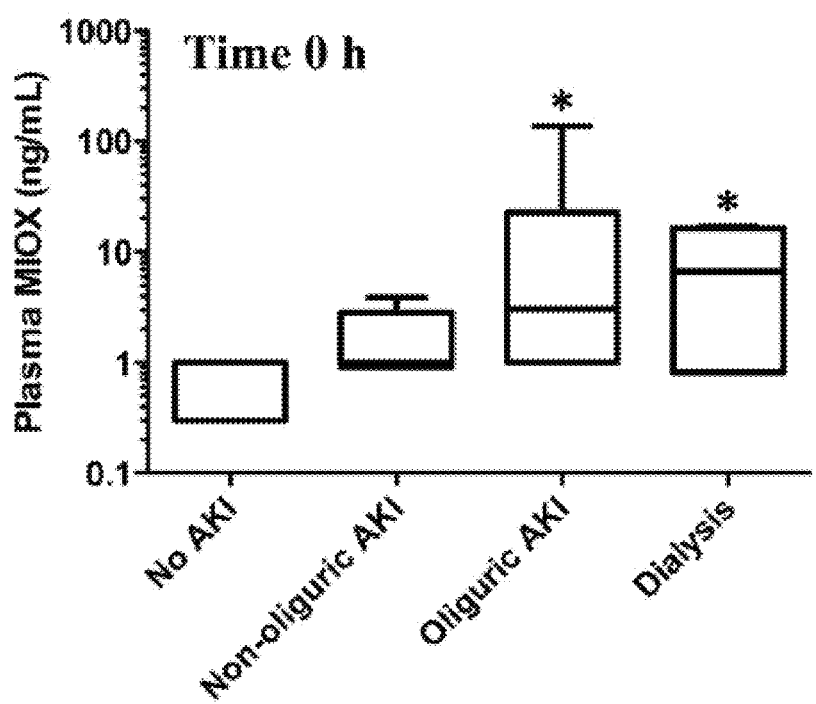
Figure 8C:
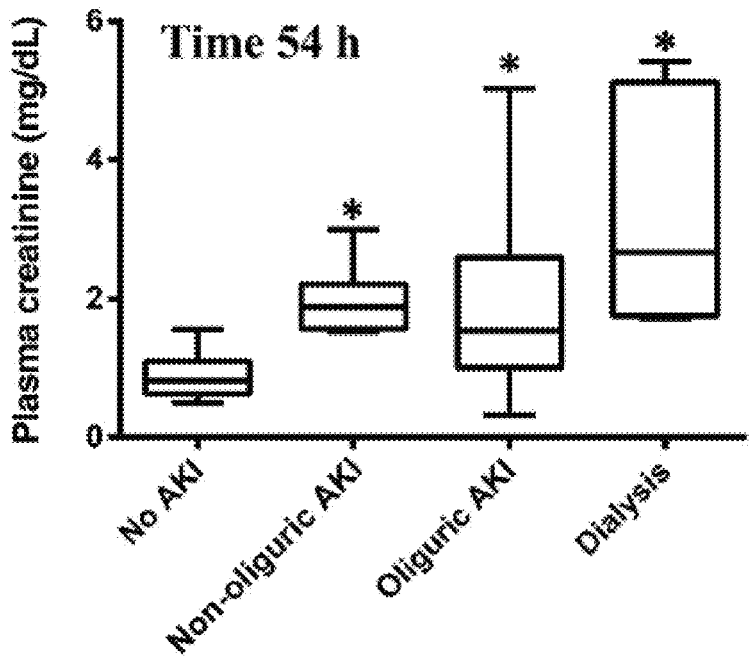
Figure 8D:
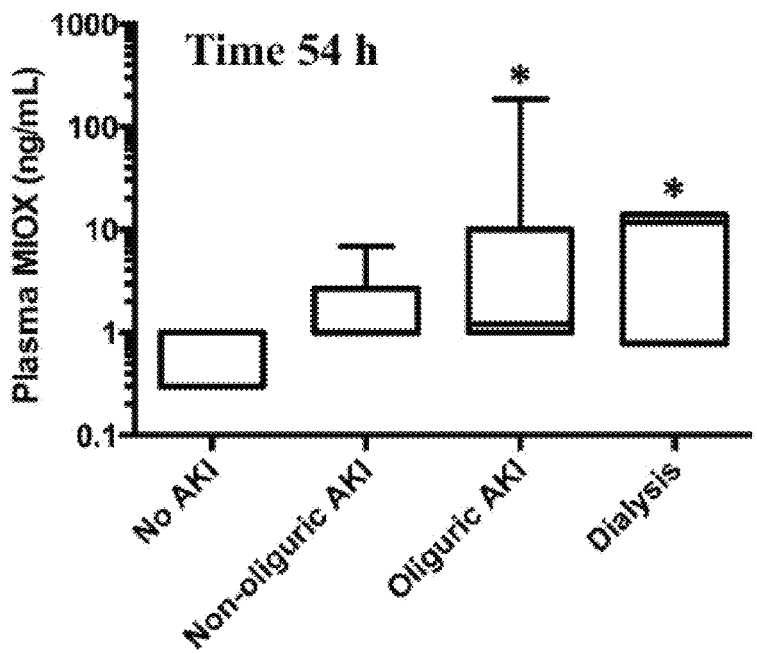
Figure 9A:
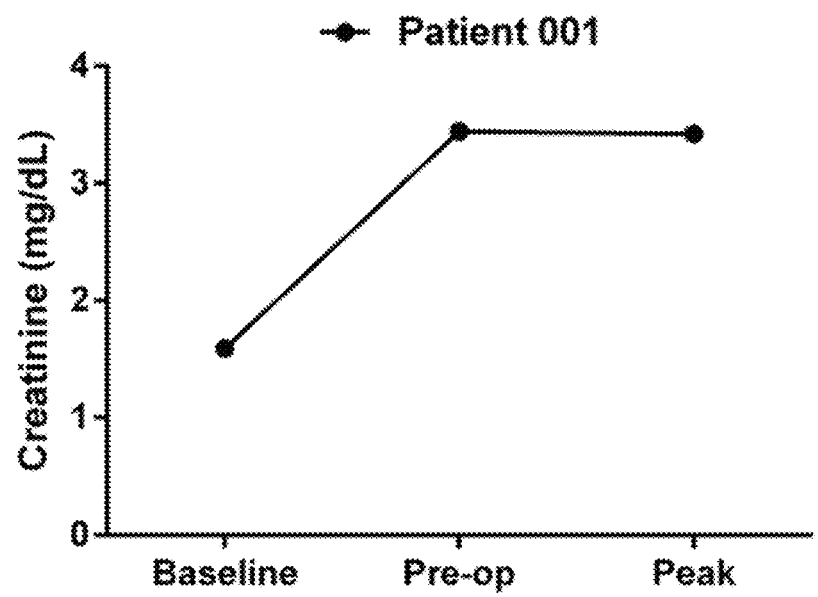
FIG. 9A, FIG. 9B, FIG. 9C and FIG. 9D depict the plasma creatinine level for four patients undergoing cardiopulmonary bypass surgery.
Figure 9B:
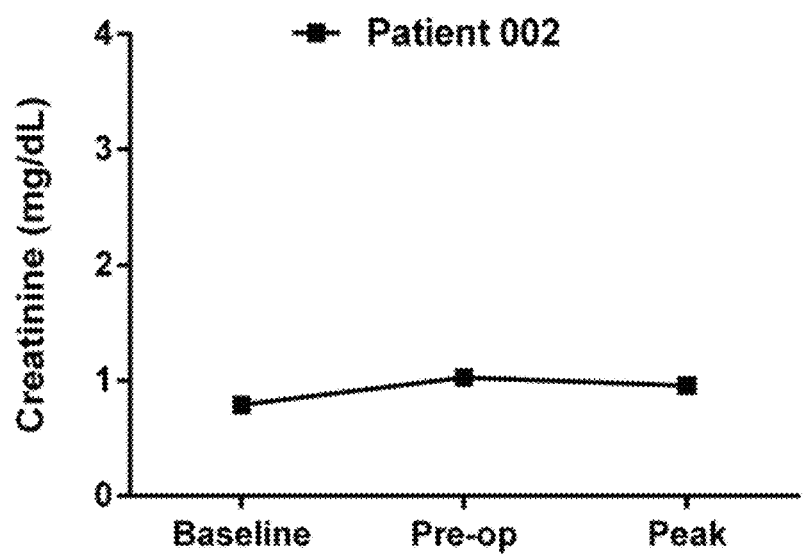
Figure 9C:
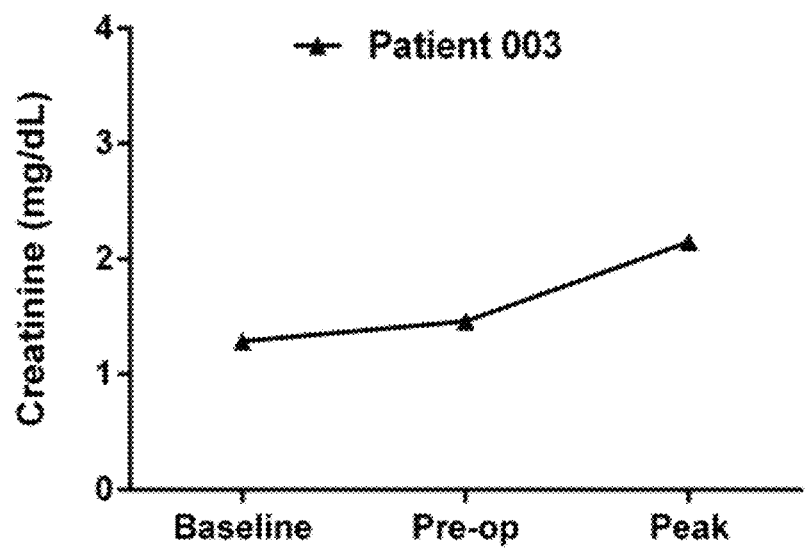
Figure 9D:
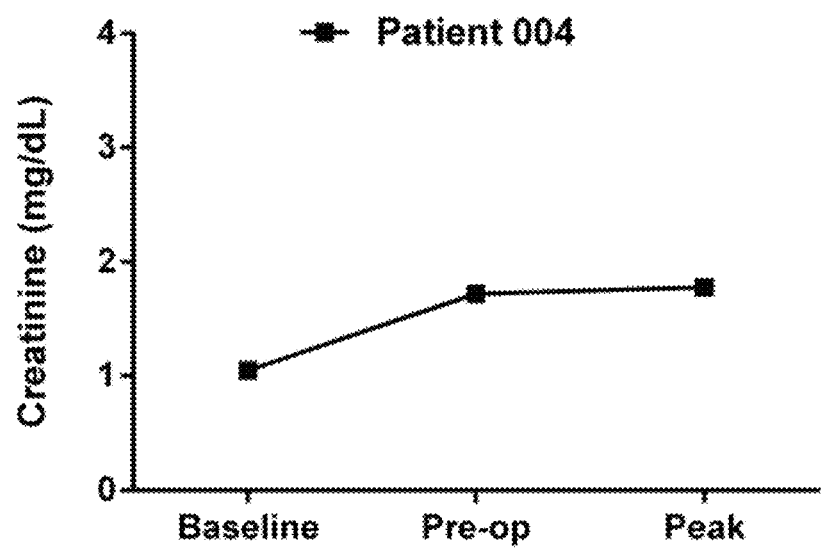
Figure 10A:
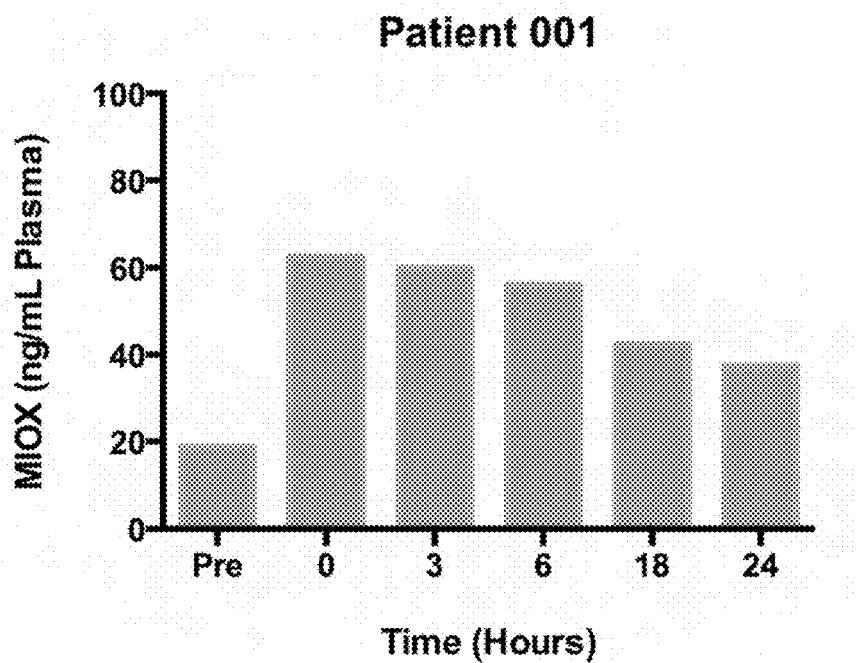
FIG. 10A, FIG. 10B, FIG. 10C and FIG. 10D depict the plasma MIOX level for four patients undergoing cardiopulmonary bypass surgery.
Figure 10B:
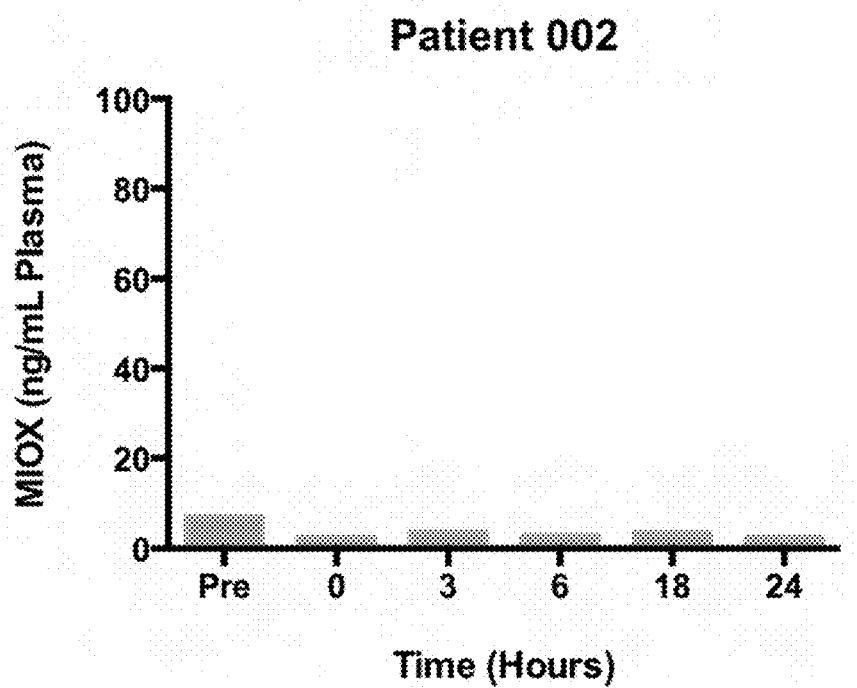
Figures 10C, 10D:
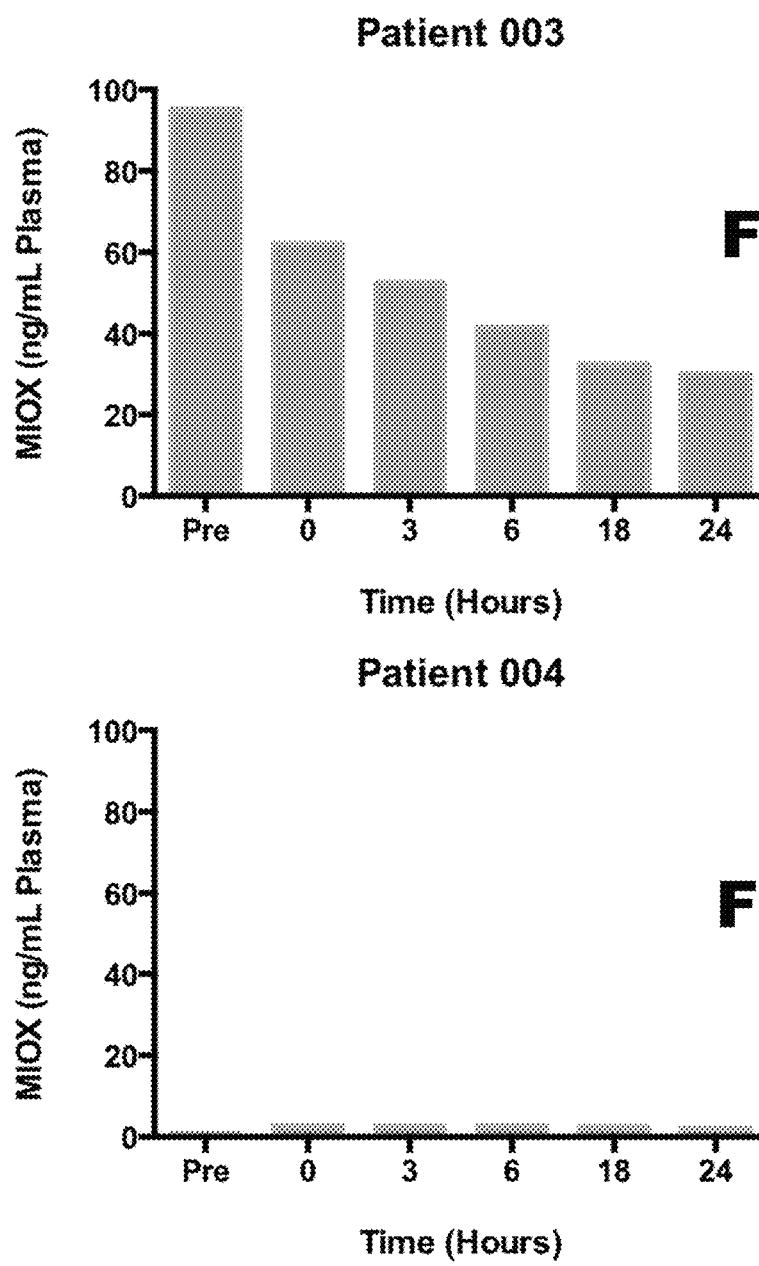

Patients in an intensive care unit (ICU) were screened for AKI, defined according to the AKIN criteria. Patients were screened for plasma creatinine increases of at least 1.5 times baseline or an absolute increase of 0.3 mg/dL (0.027 mmol/L) over a 1-3 day time period. Once a patient was identified who had an increase in plasma creatinine, remnant heparin plasma samples were collected from the Barnes Hospital Clinical Chemistry Laboratory at the time of the plasma creatinine increase and 1-3 days before the plasma creatinine increase (time 0). Plasma creatinine increased a mean (SE) of 54 (3.8) h (n=33; time 54) after the time 0 sample. The patient characteristics are summarized in Table 2. Oliguria was defined according to standard criteria as <0.5 mL/kg/h for at least 6 hours (Mehta et al. Crit Care 2007). A total of 42 patients fulfilled criteria for at least stage I AKI, defined as a relative increase in plasma creatinine of 50%, an absolute increase in plasma creatinine of 0.3 mg/dL (0.027 mmol/L), or a decrease in urine output to <0.5 mL/kg/h for at least 6 h. Of the 42 patients with AKI, 33 had increases in plasma creatinine of at least 1.5 times baseline. Nine patients had a urine output of <0.5 mL/kg/h for at least 6 h without a change in plasma creatinine. Seventeen hospitalized or critically ill patients who did not meet criteria for AKI served as controls. There was no significant difference in age between the patient groups. There was a greater proportion of male patients within the AKI group. Plasma MIOX was measured in critically ill patients with AKI at time 0 h (n=42) and time 54 h (n=37); the mean time plasma creatinine increased (FIG. 7A). Samples were not available at the time of plasma creatinine increase for 5 patients. Plasma MIOX was significantly increased in patients with AKI at time 0 [12.4 (4.3) ng/mL] and at time 54 [10.1 (5.3) ng/mL] relative to controls [0.5 (0.3) ng/mL; P=0.002] (FIG. 7B). Patients with oliguric AKI had significantly higher plasma MIOX values at time 0 [20.2 (7.5) ng/mL, n=23] and time 54 [17.1 (11.0) ng/mL, n=17] compared with controls (P<0.05) (FIG. 6). Significantly higher plasma MIOX concentrations were observed in patients with dialysis requiring AKI at time 0 [8.2 (3.5) ng/mL, n=5] and time 54 [8.2 (3.1) ng/mL, n=5] compared with controls (P<0.05) (FIG. 8A-D). All plasma MIOX concentrations were determined before initiation of dialysis. The increase in plasma MIOX preceded the increase in plasma creatinine by a mean of 54.3 (3.8) h (n=33).

Radiographic evidence of unilateral renal ischemia was available for one patient. Patient number 62 presented to the ER with chest pain. A computed tomography (CT) scan was ordered and an aortic dissection was diagnosed (FIG. 6A). This CT scan also revealed mal-perfusion of the right kidney, consistent with renal ischemia. The plasma MIOX value at the time of admission was 59.2 ng/mL. 33 hours later, the plasma MIOX value decreased to 17.0 ng/mL (FIG. 6C). In contrast, the serum creatinine at the time of admission was 1.56 mg/dL. No prior laboratory values were available for comparison. 33 hours later, the serum creatinine increased to 3.02 mg/dL (FIG. 6B).

TABLE 2

Patient characteristics.

|  | Control; No AKI (n = 17) | AKI (n = 42) | Non-oliguric AKI (n = 14) | Oliguric AKI (n = 23) | Dialysis-requiring AKI (n = 5) |
| --- | --- | --- | --- | --- | --- |
| Age (years) | 58 ± 4 | 58 ± 2 | 63 ± 4 | 56 ± 2 | 57 ± 8 |
| M:F | 8:9 | 24:18 | 7:7 | 14:9 | 3:2 |
| Race |  |  |  |  |  |
| Caucasian | 14/17 (82%) | 31/42 (74%) | 11/14 (79%) | 16/23 (70%) | 4/5 (80%) |
| African American | 2/17 (12%) | 10/42 (24%) | 2/14 (14%) | 7/23 (30%) | 1/5 (20%) |
| Hispanic | 0 | 1/42 (2%) | 1/14 (7%) | 0 | 0 |
| Unknown | 1/17 (6%) | 0 | 0 | 0 | 0 |
| Peak SCr (mg/dL) | 0.88 ± 0.08 | 2.03 ± 0.17$^a$ | 1.95 ± 0.12$^a$ | 1.81 ± 0.19$^a$ | 3.28 ± 0.78$^a$ |
| Peak BUN (mg/dL) | 16 ± 2 | 36 ± 3$^a$ | 38 ± 4$^a$ | 31 ± 2$^a$ | 57 ± 20$^a$ |

$^a$p < 0.005 compared with the control group (Kruskal-Wallis with Dunn correction for post hoc tests)
AKI—acute kidney injury;
SCr—serum creatinine;
BUN—blood urea nitrogen.

Discussion for Examples 1-6

An ideal acute kidney injury biomarker should be kidney specific, rapidly detectable following injury, correlate with the degree of tissue damage, and be easily measured. A variety of approaches have been used to identify such a biomarker. In the current study, we first sought to identify kidney specific genes. Since the proximal tubule is the major site of ischemic damage, genes specific to the proximal tubule were targeted. Using differential gene expression profiling, MIOX was identified as a renal specific proximal tubule gene. The tissue specificity was confirmed using Western blot. MIOX was localized to the proximal tubule of the kidney using immunohistochemistry. Mouse monoclonal anti-MIOX antibodies were developed and characterized. These monoclonal antibodies were optimized for use in a sandwich immunoassay to quantify MIOX in plasma. This assay was used to investigate the utility of MIOX as a biomarker of human acute kidney injury. Mice subjected to bilateral renal ischemia-reperfusion showed increased plasma MIOX 24 h postinjury. Critically ill patients with acute kidney injury showed markedly elevated plasma MIOX compared to control patients without acute kidney injury. Serum MIOX was highest in patients with oliguric and dialysis-requiring acute kidney injury. Importantly, the elevation in plasma MIOX occurred approximately 2 days prior to the elevation in plasma creatinine.

MIOX is a unique, renal specific enzyme that catalyzes the first committed step in myoinositol metabolism (Arner R J, et al. Biochem J. 2001; 360:313-320; Thorsell A G, et al. J Biol Chem. 2008; 283:15209-15216). The MIOX mRNA transcript is reportedly downregulated in a rat model of ischemic acute kidney injury (Hu et al. Am J Physiol Renal Physiol 2000; 279:F426-F439). In this study, the authors hypothesized that loss of MIOX mRNA was directly related to the degree of necrosis observed following renal ischemia. In the current study, demonstration of increased plasma MIOX following acute kidney injury may also be related to necrosis of the proximal tubule, although secretion cannot be ruled out.

It is noteworthy that MIOX was not detected in the plasma of all patients with acute kidney injury as defined using the AKIN criteria (Mehta et al.). Because the timing of renal injury was unknown in this patient population, it is possible that an increase in plasma MIOX may have occurred before or after samples were obtained. Plasma creati-nine is a nonspecific biomarker of renal injury, so it is possible that a subset of patients developed increased plasma creatinine in the absence of proximal tubule cell damage.

Other proteins have been investigated as potential kidney injury biomarkers. Previous studies have demonstrated that α-glutathione-S-transferase (α-GST), liver type fatty acid-binding protein 1 (FABP1) and N-acetyl-β-D-glucosaminidase (NAG) are detectable in urine following renal injury (Noiri E et al. Am J Physiol Renal Physiol 2009; 296:F669-F679; Westhuyzen J et al. Nephrol Dial Transplant 2003; 18:543-555). However, none of these has yet translated into clinical use. In contrast to these biomarkers, MIOX is a kidney specific protein. MIOX is also an endogenous kidney protein. Therefore, it may be released more rapidly than the inducible biomarkers KIM-1, NGAL, and FABP1. Measuring these analytes together may provide more detailed information regarding the timing of renal injury. Interestingly, MIOX did not appear to signal non-oliguric kidney injury in this retrospective study. It will be important to confirm this result in a prospective study. Nonetheless, it is most likely that a panel of biomarkers will be necessary to accurately detect AKI, determine severity, and localize the portion of the nephron injured in a given clinical scenario.

There are several limitations to this study. The human samples were collected in a retrospective manner from critically ill and hospitalized patients. The study population was screened for patients with clinical evidence of acute kidney injury and is therefore not an accurate representation of all critically ill patients. Since these samples were obtained retrospectively, they were not immediately frozen following collection. Rather, the samples were stored at 4° C. for 1-7 days prior to aliquoting and freezing. Although the MIOX immunoassay does not appear to be significantly affected by storing plasma for one week at 4° C., it is important to note that the samples were not all handled identically. This may have introduced artifact into the analysis. Previous studies confirmed the kidney-specific nature of MIOX. However, it is unknown whether MIOX expression patterns may change in other tissues following AKI or multior-gan failure. Additional studies are necessary to investigate the tissue expression profile of MIOX in these settings to explore the renal-specific nature of its origin.

In conclusion, we developed an immunoassay to quantify the kidney specific protein MIOX in human plasma. We demonstrated that plasma MIOX was elevated in animals and critically ill patients with acute kidney injury. In critically ill patients, MIOX increased approximately 2 days prior to the increase in plasma creatinine, potentially opening a therapeutic window. Additional studies are warranted to further investigate the potential of MIOX as an early biomarker of acute kidney injury.

Methods for Examples 1-6

Gene Array Analysis.

We identified kidney-specific genes according to methods described previously (Laterza et al). Briefly, brain, liver, spleen, kidney, skeletal muscle, lung, pancreas, heart, and small intestine were dissected from 3 C57Bl/6 mice and snap frozen in liquid nitrogen. Total RNA was isolated, converted into biotinylated complementary RNA (cRNA), fragmented, and applied to mouse MU75A (version 1) Genechip arrays (Affymetrix). The fluorescence intensity was scaled to 1500, and the mean difference values were calculated with Affymetrix software by measuring the difference between the perfect match and mismatch oligonucleotides. We mined these data for genes with mean difference values >10 000 in the kidney, expressed at >10-fold amounts in the kidney relative to other tissues, and expressed in the proximal tubule.

Generation and Purification of Recombinant MIOX

The nucleotide sequence for MIOX was inserted into a pGEX vector for production in *Escherichia coli*. Recombinant MIOX was purified using immobilized glutathione from Pierce according to manufacturer's instructions. Purified protein was analyzed using gel electrophoresis to confirm purity. Concentrations were determined using absorbance at 280 nm with calculated extinction coefficients from the sequence plus the GST construct or using N-terminal Edman sequencing. MIOX and GST sequences were obtained from the Swiss-Prot website (http://www.expasy.org/sprout). Recombinant GST-MIOX (absent the N-terminal methionine initiator) was cleaved with thrombin to obtain recombinant MIOX (rMIOX) protein devoid of GST. Cleaved MIOX contained an N-terminal extension of GSPEF. This material was analyzed using N-terminal Edman sequencing to confirm identity.

Anti-MIOX Antibodies

Rabbit polyclonal antibodies were produced at Harlan Bioproducts for Science (Madison, Wis.) using recombinant GST-MIOX as an immunogen. Polyclonal antibodies were purified in two steps. Cross-reacting anti-GST antibodies were first removed from sera with a GST column (#20205, Pierce) according to manufacturer's instructions. Antibodies were then affinity purified as described previously (Crimmins D, et al. Biotechnol Appl Biochem. 2010; 57:127-38). Mouse monoclonal antibodies were produced at Maine Biotechnology Services, Inc (Portland, Me.) using recombinant GST-MIOX as the immunogen and purified from cell culture media using a protein A-agarose column. Purified antibodies were dialyzed against phosphate-buffered saline, pH 7.2 containing 0.05% $NaN_3$ and quantified using absorbance at 280 nm. Monoclonal antibodies were typed using Isotyping cassettes from Pierce (#26179). Epitope mapping was performed using ABIMED spot peptide arrays prepared at the MIT Biopolymers facility as described previously (Laterza O F, et al. Clin Chem 2006; 52:1713-1721).

Western Blotting

Normal human kidney homogenate was purchased from G-Biosciences (NLH-04, G-Biosciences). Mouse and rat kidney homogenate was purchased from G-Biosciences, St. Louis, Mo. Western blotting was performed as previously described (Laterza O F, et al. Clin Chem 2006; 52:1713-1721). Blots were probed with 0.004 mg/mL of the rabbit polyclonal anti-MIOX antibody R9544 or 0.004 mg/mL of either the 01D10 or 12H06 mouse anti-MIOX monoclonal antibody. Where indicated, both monoclonal antibodies were used simultaneously, each at the above concentrations.

Immunohistochemistry

Formalin-fixed paraffin embedded human kidney tissue was obtained retrospectively from the Lauren V. Ackerman Laboratory of Surgical Pathology at Barnes Hospital. Samples were obtained from the uninvolved portions of kidneys resected for renal cell carcinoma. Single sections were stained following sodium citrate antigen retrieval using a Ventana autostainer as described previously (Gaut J P et al. Mod Pathol. 2012; November 30:epub ahead of print). A final concentration of 5 µg/mL of the rabbit polyclonal anti-MIOX antibody was used.

MIOX Immunoassay

A sandwich immunoassay was developed for MIOX using monoclonal antibody 12H06 as capture antibody and biotinylated antibody 01D10 as a capping antibody. Biotinylation of antibody 01D10 was performed using Sulfo-NHS-LC-Biotin (#21338, Pierce) according to manufacturer's instructions. The capture antibody was added to the plate at a concentration of 30 µg/mL. The capping antibody was used at a concentration of 0.33 µg/mL. Non-specific binding was blocked using Pierce Superblock (#37515, Pierce), non-specific mouse immunoglobulin G (#SLM66, Equitech-Bio, Kerryville, Tex.) and 0.5 mg/mL Tween-20 (#P-1379, Sigma-Aldrich, Saint Louis, Mo.). Plasma samples, controls, and standards were diluted 1:8 in Superblock, mouse IgG, and Tween-20 prior to analysis. GST-MIOX was serially diluted for construction of a standard curve. The concentration of GST-MIOX was set following amino acid analysis in triplicate (AAA Services Lab, Inc., Damascus, Oreg.). Streptavidin conjugated to ruthenium (#32AD, MesoScale Discovery, Rockville, Md.) was added to samples and detected using a MesoScale Discovery Sector 2400 electrochemiluminescent plate reader. Spike-recovery was determined by adding recombinant MIOX to a final concentration of either 2 ng/mL or 10 ng/mL to control human heparin plasma. Dilutional linearity was evaluated by adding recombinant MIOX to a final concentration of 5 ng/mL to 1:8, 1:16, 1:32, and 1:64 dilutions of control human heparin plasma.

Animal Model.

All animal studies were approved by the Animal Studies Committee of Washington University School of Medicine. We used C57Bl/6 mice (3 female and 4 male) ranging in age from 8 to 12 weeks. One week before surgery, serum was collected and frozen at $-80°$ C. Animals were subjected to bilateral renal ischemia for 30 min. Briefly, animals were anesthetized with a mixture of ketamine and xylazine, their body temperature was maintained at $37°$ C. on a heating pad and monitored with a rectal probe throughout surgery, and ischemia was induced by bilateral clamping of renal vascular pedicles for 30 min. Two sham-operated animals (1 male and 1 female) underwent an identical procedure without vascular pedicle clamping. Twenty-four hours after surgery, the animals were killed, serum was collected, and kidneys were perfused with 4% paraformaldehyde and placed in 4% paraformaldehyde (pH 7.4). Serum was stored at $-80°$ C. before immunoassay as described above for human plasma. We processed tissues for routine H&E staining according to standard procedures.

Human Patients.

All human studies were approved by the internal review board for human studies at Washington University School of Medicine. Patient laboratory data was screened for increases in serum creatinine occurring over a 24-72 hour time period. Patients with chronic kidney disease were not included in the study. Remnant heparin plasma samples were obtained retrospectively from the clinical chemistry laboratory of Barnes Hospital. Plasma samples were obtained before the increase in serum creatinine and at the time of the serum creatinine increase. All plasma samples were aliquoted into 500 µL aliquots and frozen at $-80°$ C. prior to analysis. Patient medical records were reviewed for demographic information, urine output, and diagnosis. Oliguria was defined as a urine output <0.5 mL/kg/h for at least 6 hours.

Statistics.

Quantitative data are presented as mean±SEM. All statistical analyses were performed using GraphPad Prism software. Comparison of individual groups of patients was evaluated using either the Mann-Whitney U Test or t test for non-parametric and parametric data, respectively. Significance was defined as $p<0.05$.

Example 7: Prospective Analysis Demonstrating MIOX as an Early Biomarker of AKI in Human Cardiac Surgery Patients 700,000 patients undergo cardiopulmonary bypass cardiac surgery in the U.S. every year. These patients have a 20-30% incidence of AKI resulting in 40% to 90% mortality. This population is ideal for study since the timing of renal injury is known. Approximately 100 adults scheduled to undergo cardiac surgery involving cardiopulmonary bypass will be enrolled. Pre-operative and post-operative blood and urine MIOX will be correlated with the current clinical standard for renal injury diagnosis (e.g., creatinine, decreased urine output, and initiation of dialysis). MIOX will be detected in blood and urine samples using an anti-MIOX antibody as described earlier. It is anticipated that plasma and urine MIOX will be detectable prior to an appreciable increase in serum creatinine. The increase in plasma and urine MIOX is anticipated to correlate with the severity of renal injury as evidenced by the degree of decrease in urine output and need for dialysis.

Samples and data have been collected for 28 patients. Patient characteristics are listed in Table 3. FIG. 9A-D shows creatinine levels in 4 patients at baseline, pre-op and at peak. FIG. 10A-D shows MIOX levels in 4 patients pre-op and 0, 3, 6, 18 and 24 hours following surgery.

TABLE 3

| Patient Characteristics | |
|---|---|
| Patient information | |
| Mean Age | 65.1 |
| % Female | 39% (11/28) |
| Race | Caucasian - 25, AA - 3 |

TABLE 3-continued

Patient Characteristics

| Patient information | |
|---|---|
| Mean serum creatinine at baseline | 1.2 mg/dL |
| Mean GFR at baseline | 64.7 mL/min |
| Diabetes | 20/28 |
| Hypertension | 27/28 |
| Congestive heart failure | 18/28 |
| Anemia | 16/28 |
| Intravenous contrast pre-op | 3/28 |
| Mean peak serum creatinine | 1.7 mg/dL |

What is claimed is:

1. An isolated antibody, wherein the antibody specifically binds myo-inositol oxygenase (MIOX) and the heavy chain comprises the amino acid sequences of SEQ ID NOs: 4, 5, and 6, and the light chain comprises the amino acid sequences of SEQ ID NOs: 1, 2, and 3; or the heavy chain comprises the amino acid sequences of SEQ ID NOs: 10, 11, and 12, and the light chain comprises the amino acid sequences of SEQ ID NOs: 7, 8 and 9.

2. The isolated antibody of claim 1, wherein the antibody comprises an amino acid sequence selected from the group consisting of SEQ ID NO:14 and SEQ ID NO:16.

3. The isolated antibody of claim 1, wherein the antibody comprises an amino acid sequence selected from the group consisting of SEQ ID NO:13 and SEQ ID NO:15.

4. The isolated antibody of claim 1, wherein the antibody is encoded by a nucleic acid sequence comprising a nucleic acid sequence selected from the group consisting of SEQ ID NO:17, SEQ ID NO:18, SEQ ID NO:19, and SEQ ID NO:20.

5. The isolated antibody of claim 1, wherein the antibody is selected from the group consisting of a single-chain antibody, an antibody fragment, a chimeric antibody, or a humanized antibody.

6. A method for measuring the amount of MIOX in a biological sample, the method comprising (i) obtaining a sample of biological fluid from a subject; and (ii) measuring the amount of MIOX in the sample by immunoassay comprising at least one isolated antibody of claim 1.

7. The method of claim 6, wherein the biological sample is a biological fluid selected from the group consisting of blood, plasma, serum and urine.

8. The method of claim 6, wherein measuring the amount of MIOX in the sample by immunoassay comprises a capture antibody and a capping antibody that specifically binds MIOX.

9. The method of claim 8, wherein the capture antibody comprises a heavy chain comprising the amino acid sequences of SEQ ID NOs: 4, 5, and 6, and a light chain comprising the amino acid sequences of SEQ ID NOs: 1, 2, and 3, and the capping antibody comprises a heavy chain comprising the amino acid sequences of SEQ ID NOs: 10, 11, and 12, and a light chain comprising the amino acid sequences of SEQ ID NOs: 7, 8, and 9.

10. The method of claim 8, wherein the capture antibody comprises a heavy chain comprising the amino acid sequences of SEQ ID NOs: 10, 11, and 12, and a light chain comprising the amino acid sequences of SEQ ID NOs: 7, 8, and 9, and the capping antibody comprises a heavy chain comprising the amino acid sequences of SEQ ID NOs: 4, 5, and 6, and a light chain comprising the amino acid sequences of SEQ ID NOs: 1, 2, and 3.

11. A method for detecting renal injury in a subject, the method comprising (i) obtaining a biological sample from a subject; (ii) measuring the amount of MIOX in the sample by immunoassay using at least one isolated antibody of claim 6; and (iii) comparing the amount of MIOX in the sample to a reference value, wherein a greater amount of MIOX in the sample compared to the reference value indicates renal injury in the subject.

12. The method of claim 11, wherein the renal injury is directly or indirectly associated with proximal tubular injury.

13. The method of claim 12, wherein the proximal tubular injury is directly or indirectly associated with proximal tubular cell damage.

14. The method of claim 11, wherein the biological sample is a biological fluid selected from the group consisting of blood, plasma, serum and urine.

15. The method of claim 11, wherein measuring the amount of MIOX in the sample by immunoassay comprises a capture antibody and a capping antibody that specifically binds MIOX.

16. The method of claim 15, wherein the capture antibody comprises a heavy chain comprising the amino acid sequences of SEQ ID NOs: 4, 5, and 6, and a light chain comprising the amino acid sequences of SEQ ID NOs: 1, 2, and 3, and the capping antibody comprises a heavy chain comprising the amino acid sequences of SEQ ID NOs: 10, 11, and 12, and a light chain comprising the amino acid sequences of SEQ ID NOs: 7, 8, and 9.

17. The method of claim 15, wherein the capture antibody comprises a heavy chain comprising the amino acid sequences of SEQ ID NOs: 10, 11, and 12, and a light chain comprising the amino acid sequences of SEQ ID NOs: 7, 8, and 9, and the capping antibody comprises a heavy chain comprising the amino acid sequences of SEQ ID NOs: 4, 5, and 6, and a light chain comprising the amino acid sequences of SEQ ID NOs: 1, 2, and 3.

* * * * *

UNITED STATES PATENT AND TRADEMARK OFFICE
CERTIFICATE OF CORRECTION

PATENT NO. : 10,060,925 B2  
APPLICATION NO. : 14/903956  
DATED : August 28, 2018  
INVENTOR(S) : Joseph P. Gaut et al.

Page 1 of 1

It is certified that error appears in the above-identified patent and that said Letters Patent is hereby corrected as shown below:

In the Specification

Column 1, Line 15 delete:
"P30 DK0793305 awarded by NIH"
And replace with:
-- DK007933 awarded by the National Institutes of Health --.

Signed and Sealed this
Fifth Day of May, 2020

Andrei Iancu
*Director of the United States Patent and Trademark Office*